US009352283B2

(12) United States Patent
Ying et al.

(10) Patent No.: US 9,352,283 B2
(45) Date of Patent: May 31, 2016

(54) TUBULAR FIBER MEMBRANE WITH NANOPOROUS SKIN

(75) Inventors: Jackie Y. Ying, Singapore (SG); Rensheng Deng, Singapore (SG); Min Hu, Singapore (SG); Ming Ni, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 385 days.

(21) Appl. No.: 13/881,705

(22) PCT Filed: Oct. 25, 2010

(86) PCT No.: PCT/SG2010/000405
§ 371 (c)(1),
(2), (4) Date: Apr. 25, 2013

(87) PCT Pub. No.: WO2012/057701
PCT Pub. Date: May 3, 2012

(65) Prior Publication Data
US 2013/0206673 A1 Aug. 15, 2013

(51) Int. Cl.
*B01D 63/02* (2006.01)
*B01D 63/06* (2006.01)
(Continued)

(52) U.S. Cl.
CPC ............ *B01D 63/02* (2013.01); *A61M 1/1621* (2014.02); *A61M 1/1625* (2014.02); *A61M 1/3689* (2014.02); *B01D 63/06* (2013.01); *B01D 67/0088* (2013.01); *B01D 69/085* (2013.01); *B01D 69/087* (2013.01); *B01D 71/68* (2013.01);
(Continued)

(58) Field of Classification Search
CPC ............ A61M 1/1621; A61M 1/3689; A61M 1/1625; B01D 2313/44; B01D 63/02; B01D 67/0088; B01D 69/085; B01D 69/087; B01D 63/06; B01D 71/68; D01D 5/06; D01D 5/247
See application file for complete search history.

(56) References Cited

U.S. PATENT DOCUMENTS 3,691,068 A 9/1972 Cross
4,906,375 A 3/1990 Heilmann
(Continued)

FOREIGN PATENT DOCUMENTS

AU 777755 B2 1/2001
CA 1 294 745 C 1/1992
(Continued)

OTHER PUBLICATIONS

Min Hu, et al., "Cell Immobilization in Gelatin-Hydroxyphenylpropionic Acid Hydrogel Fibers," Biomaterials, vol. 30, pp. 3523-3531, (Jul. 2009).
(Continued)

*Primary Examiner* — John Kim
(74) *Attorney, Agent, or Firm* — Blakely, Sokoloff, Taylor & Zafman LLP

(57) ABSTRACT

A wet spinning process for forming a tubular fiber membrane is provided. The tubular fiber membrane has a nanoporous skin layer and a microporous lumen layer. The skin layer defines an outer surface of the fiber membrane and the lumen layer defines a lumen surface of the fiber membrane. The pores in the skin layer may have an average pore size of less than about 7 nm, and pores in the lumen layer may have an average pore size of from about 0.5 to about 3 μm. The fiber membranes may be used in artificial renal proximal tubules, artificial kidneys, bioreactors, or fiber cartridges.

7 Claims, 10 Drawing Sheets

(51) Int. Cl.
| | |
|---|---|
| B01D 71/68 | (2006.01) |
| A61M 1/16 | (2006.01) |
| B01D 67/00 | (2006.01) |
| B01D 69/08 | (2006.01) |
| D01D 5/06 | (2006.01) |
| D01D 5/247 | (2006.01) |
| A61M 1/36 | (2006.01) |

(52) U.S. Cl.
CPC .................. D01D 5/06 (2013.01); D01D 5/247 (2013.01); *B01D 2313/44* (2013.01)

(56) References Cited

U.S. PATENT DOCUMENTS

| | | | | |
|---|---|---|---|---|
| 5,472,607 | A * | 12/1995 | Mailvaganam et al. | 210/490 |
| 5,549,674 | A * | 8/1996 | Humes et al. | 623/23.65 |
| 6,159,369 | A | 12/2000 | Strohm et al. | |
| 6,495,101 | B1 | 12/2002 | Yokoyama et al. | |
| 8,051,991 | B2 * | 11/2011 | Krause et al. | 210/500.23 |
| 8,496,122 | B2 * | 7/2013 | Gohl et al. | 210/500.23 |
| 8,696,909 | B2 * | 4/2014 | Luttropp et al. | 210/646 |
| 2009/0209019 | A1 | 8/2009 | Saito et al. | |
| 2010/0018394 | A1 | 1/2010 | Ekiner et al. | |
| 2010/0294714 | A1 * | 11/2010 | Buck et al. | 210/500.23 |

FOREIGN PATENT DOCUMENTS

| | | | |
|---|---|---|---|
| EP | 1 634 610 | A1 | 3/2006 |
| EP | 1875957 | A1 * | 1/2008 |
| JP | 06-292821 | A | 10/1994 |
| JP | 2004313359 | A | 11/2004 |
| SG | 80604 | A1 | 5/2001 |
| WO | WO 2008/006173 | A1 | 1/2008 |
| WO | WO 2009/108138 | A1 | 9/2009 |
| WO | WO 2010/045430 | A2 | 4/2010 |
| WO | WO 2012/057701 | | 5/2012 |

OTHER PUBLICATIONS

PCT Notification of Transmittal of the International Search Report and the Written Opinion of the International Searching Authority, or the Declaration for PCT Counterpart Application No. PCT/SG2010/000405, 8 pgs., (Jan. 4, 2011).
H. David Humes, et al., "Replacement of Renal Function in Uremic Animals with a Tissue-Engineered Kidney", Nature Biotechnology, vol. 17, pp. 451-455, (May 1999).
H. David Humes, et al., "Tissue Engineering of a Bioartificial Renal Tubule Assist Device: In Vitro Transport and Metabolic Characteristics", Kidney International, vol. 55, pp. 2502-2514, (1999).
Akira Saito, et al., "Regeneration of Peritoneal Effluent by Madin-Darby Canine Kidney Cells-Lined Hollow Fibers", Materials Science and Engineering C, vol. 6, pp. 221-226, (1998).
Akira Saito, "Research into the Development of a Wearable Bioartificial Kidney with a Continuous Hemofilter and Biofilter and Bioartificial Tubule Device Using Tubular Epithelial Cells", Artificial Organs, vol. 28, No. 1, pp. 58-63, (2004).
Rebecca H. Li, et al., "Transport Characterization of Hydrogel Matrices for Cell Encapsulation", Biotechnology and Bioengineering, vol. 50, pp. 365-373, (1996).
Rebecca H. Li, et al., "Materials for Immunoisolated Cell Transplantation", Advanced Drug Delivery Reviews, vol. 33, pp. 67-109, (1998).
Nazira Ozgen, et al., "Evaluation of Long-Term Transport Ablility of a Bioartificial Renal Tubule Device using LLC-PK$_1$ Cells", Nephrology Dialysis Transplantation, vol. 19, No. 9, pp. 2195-2207, (2004).
J. Barzin, et al., "Effect of Polyvinylpryrrolidone on Morphology and Performance of Hemodialysis Membranes Prepared from Polyether Sulfone", vol. 92, pp. 3804-3913, (2004).
P. Aebischer, et al., "The Bioartificial Kidney: Progress Towards an Ultrafiltration Device with Renal Epithelial Cells Processing", Life Support Systems; vol. 5, pp. 159-168, (1987).

Tze Kin IP, et al., "Renal Epithelial-Cell-Controlled Solute Transport Across Permeable Membranes as the Foundation for a Bioartificial Kidney", Artificial Organs, vol. 13, No. 1, pp. 59-65, (1989).
H. David Humes, et al., "Metabolic Replacement of Kidney Function in Uremic Animals with a Bioartificial Kidney Containing Human Cells", American Journal of Kidney Diseases, vol. 39, No. 5, pp. 1079-1087, (May 2002).
Sherill M. Mackay, et al, "Tissue Engineering of a Bioartificial Renal Tubule", American Society for Artificial Internal Organs Journal, vol. 44. No. 3, pp. 179-183, (1998).
H. David Humes, et al., "Initial Clinical Results of the Bioartificial Kidney Containing Human Cells in ICU Patients with Acute Renal Failure", Kidney International, vol. 56, pp. 1573-1588, (2004).
James Tumlin, et al., "Efficacy and Safety of Renal Tubule Cell Therapy for Acute Renal Failure", Journal of the American Society of Nephrology, vol. 19, pp. 1034-1040, (2008).
Yuji Fujita, et al., "Transcellular Water Transport and Stability of Expression in Aquaporin 1-Transfected LLC-PK$_1$ Cells in the Development of a Portable Bioartificial Renal Tubule Device", Tissue Engineering, vol. 10, Nos. 515, pp. 711-722, (2004).
Akira Saito, et al., "Present Status and Perspectives of Bioartificial Kidneys", The Japanese Society for Artificial Organs, vol. 9, pp. 130-135, (2006).
Yoshinobu Sato, et al., "Evaluation of Proliferation and Functional Differentiation of LLC-PK$_1$ Cells on Porous Polymer Membranes for the Development of a Bioartiticial Renal Tubule Device", Tissue Engineering, vol. 11, Nos. 9/10, pp. 1506-1515, (2006).
Mao Huijuan, et al., "Effect of Continuous Bioartificial Kidney Therapy on Porcine Multiple Organ Dysfunction Syndrome with Acute Renal Failure", American Society for Artificial Internal Organs Journal, vol. 53, No. 3, pp. 329-334, (2007).
Stefan Jockenhoevel, et al., "Fibrin Gel—Advantages of a New Scaffold in Cardiovascular Tissue Engineering", European Journal of Cardio-thoracic Surgery, vol. 19, pp. 424-430, (2001).
J. F. Mano, et al., "Natural Origin Biodegradable Systems in Tissue Engineering and Regenerative Medicine: Present Status and Some Moving Trends", Journal of the Royal Society Interface, vol. 4, pp. 999-1030, (2007).
Anita Mol, et al., "Fibrin as a Cell Carrier in Cardiovascular Tissue Engineering Applications", Biomaterials, vol. 26, pp. 3113-3121, (2005).
Qing Ye, et al., "Fibrin Gel as a Three Dimensional Matrix in Cardiovascular Tissue Engineering", European Journal of Cardio-thoracic Surgery, vol. 17, pp. 587-591, (2000).
R. Büttemeyer, et al., "In a Pig Modei ePTFE Grafts will Sustain for 6 Weeks a Confluent Endothelial Cell Layer Formed in Vitro under Shear Stress Conditions", Eur. J. Vasc. Endovasc. Surg., vol. 26, pp. 156-160, (2003).
T. R. Dunkern, et al., "A Novel Perfusion System for the Endothelialisation of PTFE Grafts Under Defined Flow", Eur. J. Vasc. Endovasc. Surg., vol. 18, pp. 105-110, (1999).
Tze Kin IP, et al., "Cellular Control of Membrane Permeability. Implications for a Bioartificial Renal Tubule", ASAIO Transactions, vol. 34, pp. 351-355, (1988).
Qian Yang, et al., "Tailoring Pore Size and Pore Size Distribution of Kidney Dialysis Hollow Fiber Membranes via Dual-Bath Coagulation Approach", Journal of Membrane Science, vol. 290, pp. 153-163, (2007).
Elizabeth Arkhangelsky, et al., "Hypochlorite Cleaning Causes Degradation of Polymer Membranes", Tribology Letters, vol. 28, pp. 109-116, (2007).
Yi Duan, et al., "Shear-Induced Reorganization of Renal Proximal Tubule Cell Actin Cytoskeleton and Apical Junctional Complexes", PNAS, vol. 105, No. 31, pp. 11418-11423, (Aug. 12, 2008).
Marie Essig, et al., "Mechanical Strains Induced by Tubular Flow Affect the Phenotype of Proximal Tubular Cells", Am. J. Physiol. Renal. Physiol., vol. 281, pp. F751-F762, (2001).
Kyung-Jin Jang, et al., "A Multi-Layer Microfluidic Device for Efficient Culture and Analysis of Renal Tubular Cells", Lab Chip, vol. 10, No. 1, pp. 36-42, (Jan. 7, 2010).
Huishi Zhang, et al., "The Impact of Extracellular Matrix Coatings on the Performance of Human Renal Cells Applied in Bioartificial Kidneys", Biomaterials, vol. 30, pp. 2899-2911, (2009).

(56) References Cited

OTHER PUBLICATIONS

Matthias Wieser, et al., "hTERT Alone Immortalilzes Epithelial Cells of Renal Proximal Tubules without Changing their Functional Characteristics", Am. J. Physiol. Renal. Physiol., vol. 295, pp. F1365-F1375, (2008).

Peter M. T. Deen, et al., "Apical and Basolateral Expression of Aquaporin-1 in Transfected MDCK and LLC-PK Cells and Functional Evaluation of their Transcellular Osmotic Water Permeabilities", Pflügers. Arch.—Eur. J. Physiol., vol. 433, pp. 780-787, (1997).

PCT Notification of Transmittai of the International Search Report Searching Authority, or the Declaration for related PCT Application No. PCT/SG2010/000173, 13 pgs., (Jul. 29, 2010).

Farah Tasnim, et al., "Achievements and Challenges in Bioartificial Kidney Development", Fibrogenesis & Tissue Repair, vol. 3, No. 14, pp. 1-12, (2010).

PCT Notification concerning Transmittal of International Preliminary Report on Patentability (Chapter I of the Patent Cooperation Treaty) for PCT Counterpart Application No. PCT/SG2010/000405, 5 pgs., (May 10, 2013).

* cited by examiner

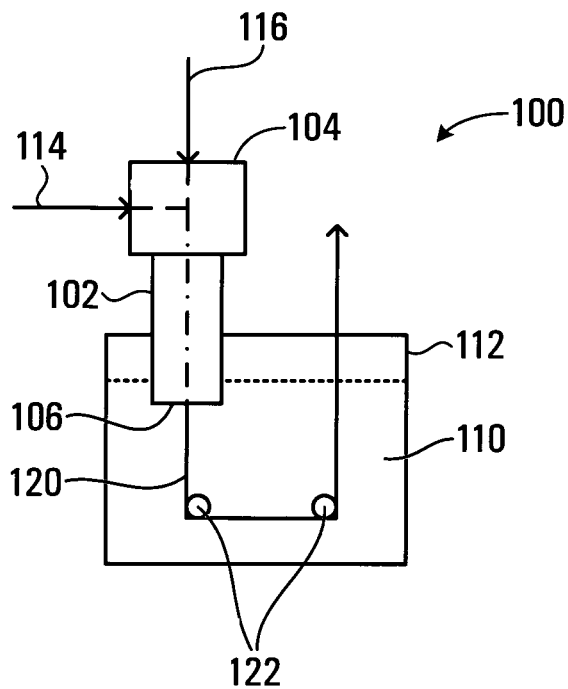
FIG. 1A
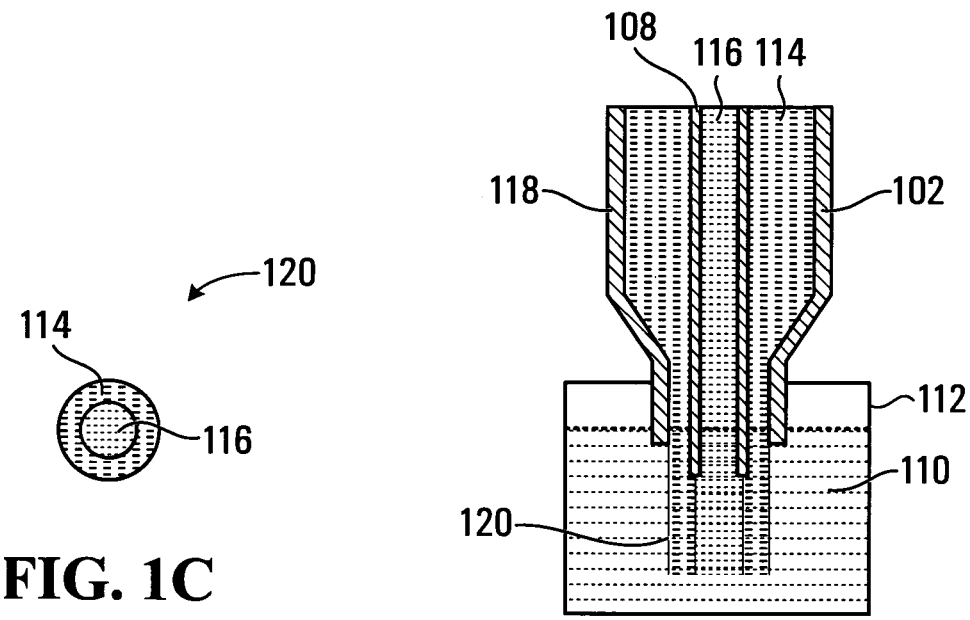
FIG. 1C
FIG. 1B

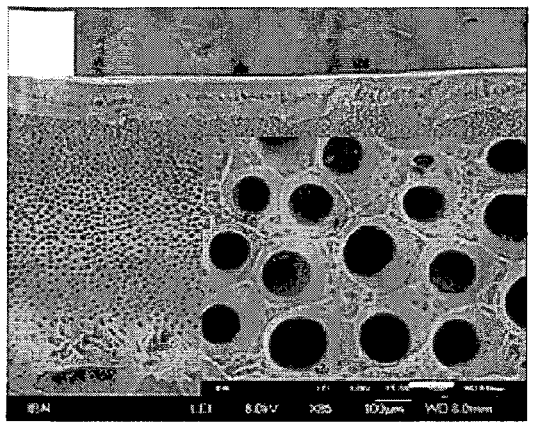 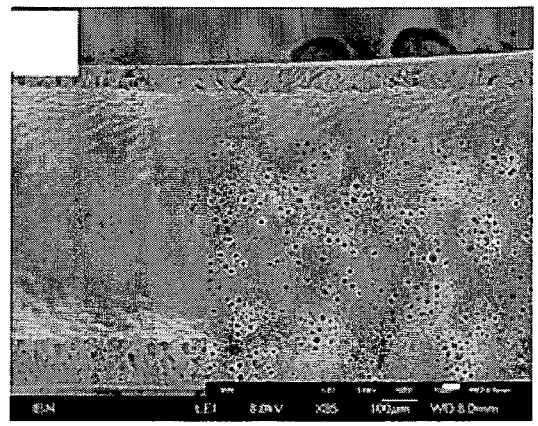
FIG. 6A  FIG. 6B
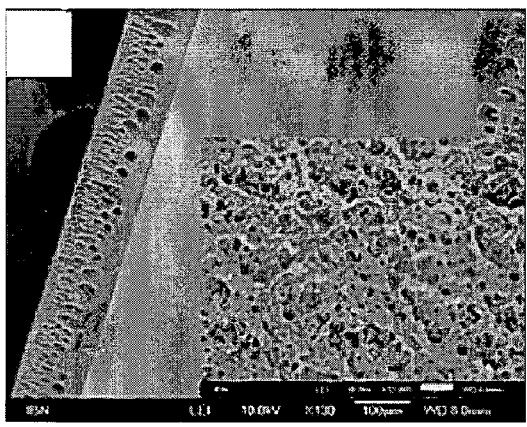 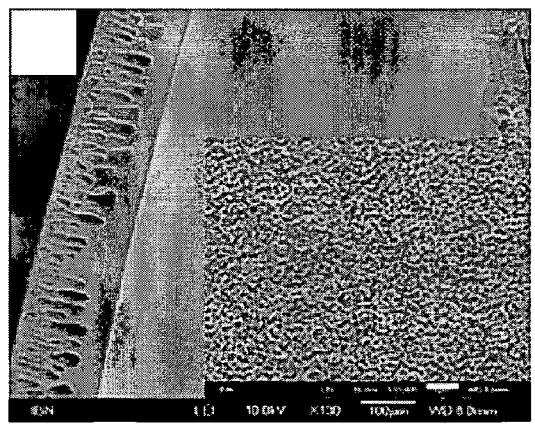
FIG. 6C  FIG. 6D

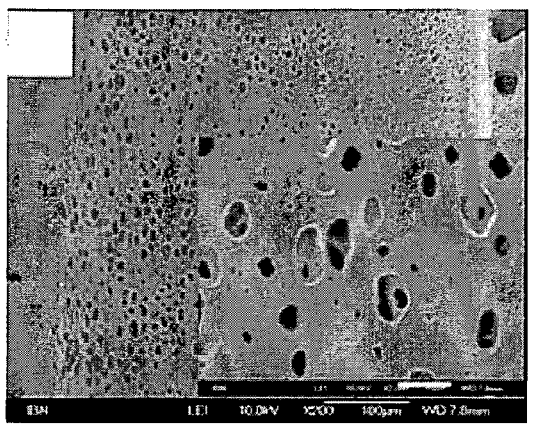
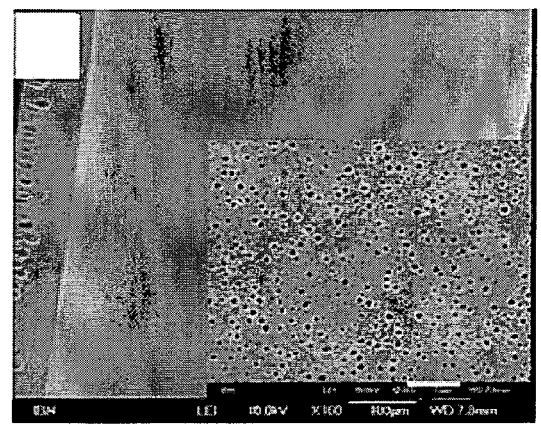
FIG. 7AFIG. 7B
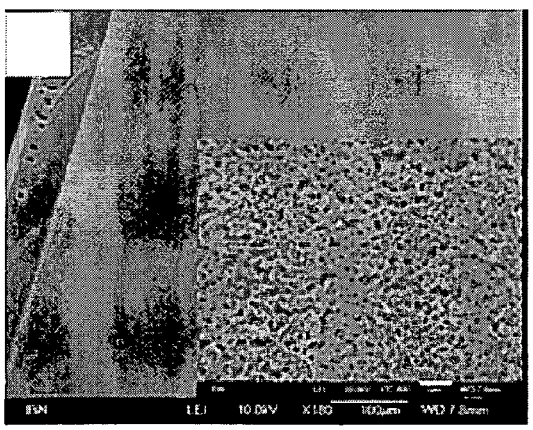
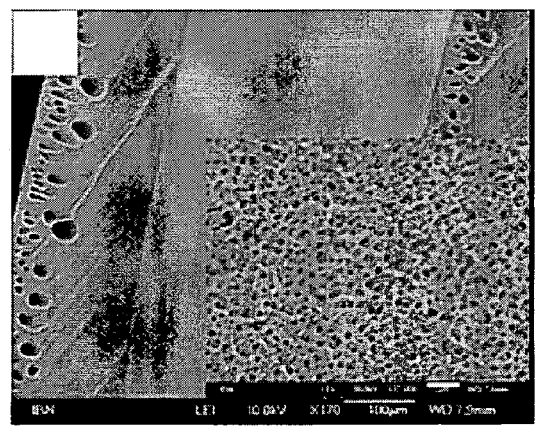
FIG. 7CFIG. 7D

TUBULAR FIBER MEMBRANE WITH NANOPOROUS SKIN

CROSS-REFERENCE TO RELATED APPLICATION

This patent application is a U.S. National Phase Application under 35 U.S.C. § 371 of International Application No. PCT/SG2010/000405, filed Oct. 25, 2010, entitled TUBULAR FIBER MEMBRANE WITH NANOPOROUS SKIN.

FIELD OF THE INVENTION

The present invention relates generally to tubular fiber membranes, and particularly to fiber membranes for use in artificial renal proximal tubules, artificial kidneys, and bioreactors, and related methods and processes.

BACKGROUND OF THE INVENTION

Artificial renal tubule can be used in renal substitution therapy. For example, bioartificial renal tubule assist devices (RAD) have been developed and tested, which utilizes hemodialysis hollow fiber membranes. Generally, these fiber membranes are suitable for hemofiltration or hemodialysis.

An asymmetrical microporous hollow fiber for hemodialysis is described in U.S. Pat. No. 4,906,375 to Heilmann, issued Mar. 6, 1990 (referred to herein as "Heilmann"). The fiber has an inner barrier layer and an outer foam-like supporting structure, and is formed of a hydrophobic organic polymer. The hydrophobic organic polymer may be polysulfones such as polyethersulfones (PES). The outer supporting structure is a supporting membrane with a substantially larger pore size than that of the inner barrier layer. The fiber is formed using a spinning system as described in U.S. Pat. No. 3,691,068 to Cross, issued Sep. 12, 1972 (referred to herein as "Cross"). In particular, a casting solution is introduced into a nozzle or spinneret with a precipitating liquor. The casting solution contains the hydrophobic organic polymer, a hydrophilic polymer such as polyvinyl pyrrolidone (PVP), and an aprotic solvent such as N-methylpyrrolidone (NMP). The precipitating liquor may contain NMP and a non-solvent such as water. The casting solution and the precipitating liquor are passed through the spinneret simultaneously and the extruded fiber is precipitated from the inside to the outside. The extruded fiber is passed into a washing bath, where the upper surface of the washing bath is separated from the spinneret by an air gap. The air gap is provided so that full precipitation of components has occurred before the precipitated polymer solution enters the washing bath. The spinning process described in Heilmann and Cross is known in the art as dry-wet spinning, or gel spinning.

US 2009/0209019 to Saito et al., published Aug. 20, 2009 (referred to herein as "Saito"), discloses a bioartificial renal tubule suitable for continuous hemofiltration. The bioartificial renal tubule includes an artificial membrane having an inner surface coated with renal tubular epithelial cells. The hollow fiber membrane has uniformly distributed micropores, and may include polysulfone, polyethersulfoner, polyacrylonitrile, polyvinyl alcohol, and cellulose acetate. An extracellular matrix may be attached to the hollow fiber, which includes collagen I, collagen IV, laminin, fibronectin, and Pronectin.

EP 1634610 to Mabuchi et al., published Mar. 15, 2006 (referred to herein as "Mabuchi"), discloses a polysulfone-based hollow fiber membrane with selective permeability. Mabuchi teaches that the average open pore area on the outer surface of the hollow fiber membrane is preferably 0.3 to 1.0 $\mu m^2$. Mabuchi discloses that fiber membranes are formed by simultaneously extruding a membrane-forming solution and an interior-coagulation solution, through a nozzle, passing the extruded solution through an air gap, and then coagulating the solution in an aqueous solution.

In the development of artificial renal tubule devices reported in the literature, it is typical to seed cells in hollow fiber membranes as follows. The lumen surface of the hollow fiber is first coated with an extracellular matrix (ECM), and a cell-suspended solution is next introduced into the fiber lumen. After an extended period (typically hours), the cells will settle down under gravity and attach to the ECM-coated bottom surface. The fiber needs to be rotated after a seeding period, e.g. by 90 degrees, to seed another side of the lumen surface. In this technique, four seeding periods are typically required to seed cells on all sides of the lumen surface.

SUMMARY OF THE INVENTION

It has been realized that fiber membranes suitable for hemofiltration or hemodialysis may not be suitable for reabsorption or for use as artificial renal proximal tubules. In particular, when the pore sizes in fiber membranes used in reabsorption processes are larger near the outer surface than near the inner (lumen) surface of the fiber membranes, some materials, such as healthy blood cells or proteins, may be trapped in the membrane, thus clogging the pores and reducing performance over time.

It has also been realized that when cells are seeded in conventional fiber membranes using the cell seeding technique discussed above, particularly with four rotations and four seeding periods, the seeded cells are not distributed uniformly on the lumen surface. Increasing the number of rotations and seeding periods can increase the uniformity of cell distribution, but also substantially increase the seeding time.

Thus, in accordance with an aspect of the present invention there is provided a method of forming a fiber membrane. This method utilizes a fiber-forming solution, a lumen-defining fluid, a coagulation bath, and a spinneret for forming a tubular fiber. The fiber-forming solution comprises a solvent, a hydrophobic polymer dissolved in the solvent, and a hydrophilic polymer. The coagulation bath comprises less than 50 v % of the solvent and more than 50 v % of a non-solvent. The spinneret has an exit in contact with the coagulation bath so that an extruded material exiting from the exit will enter the coagulation bath without being exposed to the air. The method comprises co-extruding the fiber-forming solution and the lumen-defining fluid through the spinneret and the exit, and precipitating the extruded fiber-forming solution in the coagulation bath without exposing the extruded fiber-forming solution to the air, to form a porous tubular fiber membrane comprising a nanoporous skin layer and a microporous lumen layer. The concentrations of the solvent and the non-solvent in the coagulation bath are selected to control pore sizes in the skin layer of the fiber membrane. The concentrations of the solvent and the non-solvent in the coagulation bath may be selected so that pores in the skin layer have an average pore size of less than about 7 nm. The lumen-defining fluid may be selected to control pore sizes in the lumen layer, such that pores in the lumen layer have an average pore size of about 0.5 to about 3 µm. The non-solvent may comprise water, the solvent may comprise. N-methyl-2-pyrrolidone (NMP), the hydrophobic polymer may comprise polyethersulfone (PES), and the hydrophilic polymer may comprise polyvinyl pyrrolidone (PVP). The fiber-forming solution may comprise about 16 to about 20 wt % of the hydrophobic polymer, about 8 to about 10 wt % of the hydrophilic polymer, and about 72 to about 74 wt % of the solvent; and the coagulation bath may comprise about 10 v % of the solvent and about 90 v % of the non-solvent. The lumen-defining fluid may comprise about 60 to about 90 v % of the solvent and about 40 to about 10 v % of the non-solvent. The lumen-defining fluid may comprise oil. A layer of hydrogel may be formed on the lumen layer. The hydrogel may comprise fibrin. The method may comprise attaching cells to the hydrogel to allow the cells to attach to the lumen layer. The hydrogel may be degraded and removed and the cells may be cultured to form a confluent monolayer of the cells on the lumen layer. The cells may comprise human renal proximal tubule epithelial cells.

In accordance with another aspect of the present invention, there is provided an artificial renal proximal tubule, comprising a tubular fiber membrane defining a lumen, the fiber membrane comprising a nanoporous skin layer and a microporous lumen layer, the skin layer defining an outer surface of the fiber membrane and the lumen layer defining a lumen surface of the fiber membrane. The pores in the skin layer may have an average pore size of less than about 7 nm, and pores in the lumen layer may have an average pore size of from about 0.5 to about 0.3 μm. The fiber membrane may comprise polyethersulfone (PES). The artificial renal proximal tubule may comprise a layer of hydrogel formed on the lumen layer. The hydrogel may comprise fibrin. Cells may be attached to the lumen layer. The cells comprise human renal proximal tubule epithelial cells.

In accordance with a further aspect of the present invention, there is provided an artificial kidney comprising the artificial renal proximal tubule described herein.

In accordance with another aspect of the present invention, there is provided a cartridge. The cartridge comprises a body defining a fluid chamber, a plurality of tubular fiber membranes mounted on the body and passing through the fluid chamber, each one of the tubular membranes defining a lumen, at least one of the tubular fiber membranes comprises a nanoporous skin layer and a microporous lumen layer, the skin layer defining an outer surface of the at least one tubular fiber membrane and the lumen layer defining a lumen surface of the at least one tubular fiber membrane; a conduit in fluid communication with lumens of the tubular fiber membranes; and a conduit in fluid communication with the fluid chamber. A first conduit may be provided in the cartridge for fluid communication with a first end of the lumens of the tubular fiber membranes, a second conduit may be provided for fluid communication with a second end of the lumens of the tubular fiber membranes, and third and fourth, conduits in fluid communication with the fluid chamber.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention, FIG. 1A is a schematic diagram of a wet spinning system in operation, exemplary of an embodiment of the present invention;

FIG. 1B is a schematic cross-sectional view of the fluid flow during the operation of the system of FIG. 1A;

FIG. 1C is a cross-sectional elevation view of an exemplary spinneret-bath configuration;

FIGS. 6A, 6B, 6C, 6D, 7A, 7B, 7C, and 7D are SEM images of sample fibers;

DETAILED DESCRIPTION

Figure 2:
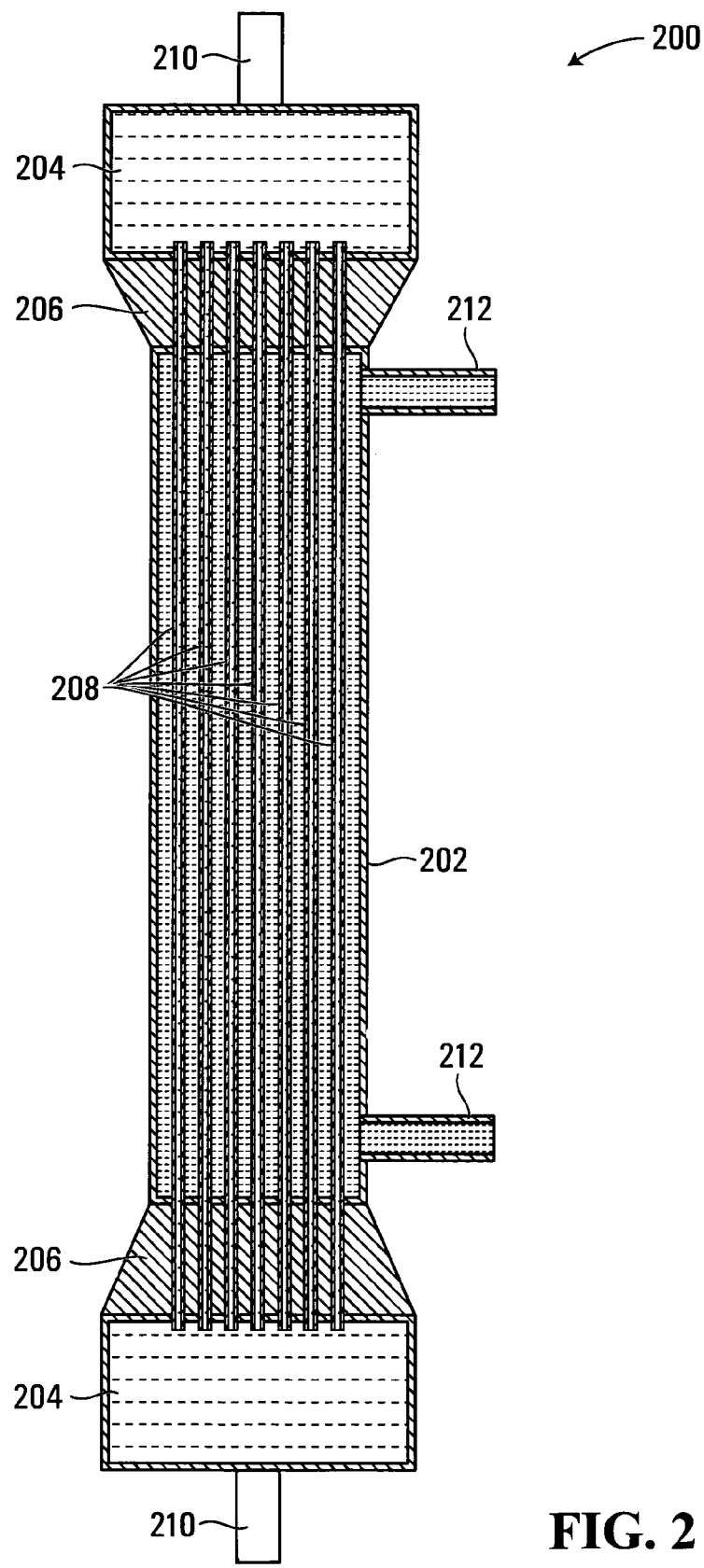
FIG. 2 is a view of a cartridge, exemplary of an embodiment of the present invention.

An exemplary embodiment of the present invention relates to a method of forming a porous tubular fiber membrane according to a technique known as wet spinning. The method is illustrated in FIGS. 1A, 1B, and 1C, which schematically depicts an exemplary wet spinning apparatus 100. It should be understood that a different wet spinning systems may be used to perform this method.

Apparatus 100 includes a spinneret 102, which has an inlet end 104 and an exit end 106. Spinneret 102 is structured to receive a plurality of fluids to form generally coaxial laminar flows of the fluids. Spinneret 102 can be any suitable spinneret for wet spinning a solution to form a tubular fiber, and can be readily designed and constructed by those skilled in the art in view of the description herein. Some spinnerets described in the literature may be used with or without modification. For example, the spinneret may be adapted or modified from spinnerets disclosed in Cross, Hu et al., "Cell immobilization in gelatin-hydroxyphenylpropionic acid hydrogel fibers," *Biomaterials*, 2009, vol. 30, pp. 3523-31 (referred to herein as "Hu et al."), and WO/2009/108138 to Ying et al., published Mar. 9, 2009 (referred to herein as "Ying"). Exit end 106 is immersed, in, and in contact with, a coagulation bath 110 contained in a container 112 so that there is no air gap between exit end 106 and coagulation bath 110. An extruded material exiting from exit end 106 will thus enter coagulation bath 110 without being exposed to the air.

In operation, a fiber-forming solution 114 (also referred to herein as "dope solution") and a lumen-defining fluid 116 (also referred to herein as "core solution") are fed into spinneret 102 through inlet end 104 at selected flow rates. Spinneret 102 shapes solution 114 and fluid 116 to form a generally coaxial laminar flow 120.

As schematically illustrated in FIG. 1B, spinneret 102 may have a core tubing 108 that defines a core channel for receiving and extruding a core solution, and an outer duct 118 that defines an outer channel for receiving and extruding a dope solution.

To better illustrate the precipitation process, FIG. 1B shows a partial schematic cross-sectional view of an exemplary spinneret/bath configuration. As depicted, fiber-forming solution 114 (dope solution) is extruded from the outer channel of the spinneret 102, and lumen-defining fluid 116 (core solution) is extruded from the core channel of the spinneret 102. Solutions 114 and 116 are simultaneously extruded through spinneret 102 and exit end 106.

After extrusion, the lumen-defining fluid 116 flows in the central region and the fiber-forming solution 114 flows on the outside around the lumen-defining fluid 116, as shown in FIGS. 1B and 1C. As there is no air gap between the exit end 106 of spinneret 102 and coagulation bath 110, the extruded laminar flow 120 is introduced into Coagulation bath 110 without being exposed to the surrounding air.

Fiber-forming solution 114 contains a solvent, a hydrophobic polymer dissolved in the solvent, and a hydrophilic polymer. Coagulation bath 110 contains the solvent and a non-solvent. The non-solvent may be water. The components of the fiber-forming solution 114 and the coagulation bath 110 are selected so that the hydrophilic polymer in the fiber-forming solution 114 will precipitate when the fiber-forming solution 114 is extruded into and contacts coagulation bath 110, so as to form a desired tubular fiber membrane.

In some embodiments, the lumen-defining fluid 116 may also contain a coagulation solution which can precipitate the fiber-forming solution 114 through the interface between fiber-forming solution 114 and the lumen-defining fluid 116.

For reasons to be discussed below, the coagulation bath 110 contains more than 50 v % of the non-solvent and less than 50 v % of the solvent, and, when the lumen-defining fluid 116 is a coagulation solution, the coagulation solution contains more than 50 v % of the solvent and less than 50 v % of the non-solvent.

In a specific embodiment, the solvent is N-methyl-2-pyrrolidone (NMP), the hydrophobic polymer is polyethersulfone (PES), and the hydrophilic polymer is polyvinyl pyrrolidone (PVP). The fiber-forming solution 114 may contain about 16 to about 20 wt % of PES, about 8 to about 10 wt % of PVP, and about 72 to about 74 wt % of NMP. The coagulation bath 110 may contain about 10 v % of NMP and about 90 v % of water. The lumen-defining fluid 116 may contain oil, or may contain about 60 to about 90 v % of NMP and about 40 to about 10 v % of water.

In other embodiments, other suitable combinations of polymers, solvents, and non-solvents may be selected.

In particular, other hydrophobic polymers that can be used to produce membranes with nanopores in a phase inversion manufacture process may be used. For example, potentially suitable hydrophobic polymers include polysulfones, such as polyethersulfones and polymeric aromatic polysulfones; poly(vinylidene fluoride) (PVDF); polyetherimides (PEI); polyacrylonitriles (PAN); polyimides; and celluloses. Polyvinyl chlorides (PVC), polycarbonates, polyamides such as polyhexamethyleneadipamides, and polymers of modified acrylic acids and halogenated polymers may also be used in some applications. Mixtures of two or more of the above polymers may also be used.

Potentially suitable hydrophilic polymers include PVP, polyethyleneglycol (PEG), polyacryl acids, polyvinyl-alcohols, and polyvinyl acetates. Other hydrophilic polymers such as polyglycol monoesters; copolymers of polyethyleneglycols with polypropyleneglycol; polysorbates such as polyoxyethylenesorbitane monooleate, monolaurate, or monopalmitate; water soluble cellulose derivatives such as carboxymethylcellulose, or cellulose acetate; or the like may also be used in some applications.

Potentially suitable solvents include dimethylformamide (DMF), dimethylsulfoxide (DMSO), dimethylacetamide (DMA), NMP, or mixtures thereof. Other polar, aprotic solvents may also be used.

When selecting the chemicals to be used in the formation process, care should be taken to ensure that the particular combination of chemicals selected can produce the desired pore sizes under suitable conditions, and that the resulting fibers will have suitable mechanical, chemical and biological properties as required or desired for the particular application in which the fibers are to be used.

For example, in some cases, the produced fibers may have macrovoids (voids that are larger than about 10 µm) in the membrane wall. These macrovoids may decrease the mechanical strength of the hollow fiber. Thus, in some embodiments, it may be desirable to reduce or limit the number or size of macrovoids in the fibers. One factor that can impact on the formation of the macrovoids is the combination of polymers and solvents used.

For a given combination of polymers and solvents, the volume of macrovoids may be reduced by increasing the concentration of the hydrophobic polymer in the dope solution, or the viscosity of the dope solution. Thus, in applications where a large volume of macrovoids is not desirable or certain mechanical strength of the fiber is desired, the polymer concentration in the dope solution should be sufficiently high. Further, it is expected that when the molecular weight of the hydrophobic polymer is higher, the size and volume of macrovoids will be smaller. When the dope solution includes a higher content of the hydrophilic polymer, such as PVP, the size and volume of the macrovoids may be decreased. Thus, in cases where it is desirable to limit the size and volume of the macrovoids, the concentration of the hydrophilic polymer in the dope solution should be sufficiently high. As a high molecular weight of the hydrophilic polymer may increase the overall viscosity of the dope solution, using a hydrophilic polymer with a higher molecular weight may also help to control the formation of macrovoids in the fibers.

The fiber-forming solution 114 may be formed by mixing the desired components to form a mixture and the mixture may be stirred to form a homogeneous dope solution.

When PES, PVP and NMP are used in the dope solution, the concentrations of PES and PVP in the dope solution may vary in the ranges of about 15 to about 25 wt % (PES) and about 5 to about 15 wt % (PVP) respectively. Suitable PES may have an average molecular weight (Mw) above 30 kDa, such as about 51 kDa. Suitable PVP may have an Mw in the range of 10 to about 400 kDa, such as about 25 kDa. In some embodiments, depending on the desired pore size distribution, the PES used in the dope solution may have a molecular weight cutoff at about 60 kDa so that a sufficiently high concentration of PES can be dissolved in the dope solution, to provide the desired pore size distribution.

The lumen-defining fluid 116 may be a liquid that is immiscible and biocompatible with the dope solution. For example, when the dope solution is formed of PES, PVP and NMP, or an aqueous solution, a biocompatible oil, such as FC3283 oil provided by 3M™ may be used as the lumen-defining fluid 116. FC3283 oil is immiscible with water and NMP, and has a density of 1820 kg/m$^3$ and a viscosity of 1.4 cp.

For convenient processing, the density of lumen-defining fluid 116 should be higher than the density of the coagulation bath, so that the hollow fiber formed in the bath will fall downward in the bath. However, the lumen-defining fluid 116 should not be too heavy, to avoid exerting an excessive force on the extruded fiber. In some embodiments, the density of lumen-defining fluid 116 may be from about 1000 to about 2000 kg/m$^3$.

The viscosity of the lumen-defining fluid 116 should be relatively low, such as in the range from about 1 to about 3 cp.

The lumen-defining fluid 116 may be a mixture of different components at a selected ratio. For example, the mixture may be a mixture of a solvent and a non-solvent, such as NMP and water; a mixture of different non-solvents, such as isopropanol (IPA) and water; or a mixture of a solvent, a non-solvent, and a hydrophilic polymer such as PVP or PEG.

Potentially suitable non-solvents include water, IPA, alcohols such as ethanol and butanol, or the like.

The coagulation bath 110 may contain from about 0 to about 30 vol % of the solvent, such as NMP. As noted elsewhere, when the ratio of solvent to non-solvent in the bath is increased, the pore sizes in the fibers may increase. Thus, the concentration of the solvent, or the ratio of solvent to non-solvent in the bath should be limited to control the pore size distribution in the fibers.

After the fiber-forming solution 114 enters coagulation bath 110, it is contacted by coagulation bath 110 on the outside and starts to precipitate inward from the outer surface. As the coagulation bath is selected and configured to control the pore sizes in the skin layer of the formed tubular fiber membrane, the skin layer is nanoporous. In particular, without being limited to any particular theory, it is expected that when precipitation occurs in the presence of relatively higher content of the non-solvent, smaller pores tend to form; and when there is a relatively higher content of the solvent, larger pores tend to form. On the other hand, the lumen layer of the tubular fiber membrane is microporous, as the inner surface of fiber-forming solution 114 is in contact with the lumen-defining fluid 116, which has no, or a low concentration of, the non-solvent.

In other words, and without being limited to any particular theory, it is expected that after extrusion, the dope solution comes into contact with both the core solution and the coagulation bath. Upon on contact, the solvent (e.g. NMP) initially in the dope solution starts to move out of the dope solution and into the core solution or the bath, and non-solvent (e.g. water) starts to move in the opposite direction. This solvent/non-solvent exchange results in the formation of very small pores at or near the interface between two adjacent liquids, and the formation of large pores away from the interfacial region. Therefore, to form smaller pores in the skin layer and larger pores in the lumen layer, the spinneret and the bath in this embodiment is arranged to allow the outer surface of the dope solution to come into contact with the bath before the inner surface of the dope solution comes into contact with the core solution. As can be understood by those skilled in the art, such results may be achieved by using a spinneret configuration as illustrated in FIG. 1B, or a suitably modified spinneret, and immersing the exit end of the spinneret in the bath.

If there is an air gap between the spinneret and the bath, particularly if the air gap is large, the dope solution would then contact the core solution first and the bath sometime later. This would result in larger pores in the skin layer and smaller pores in the lumen layer.

In addition, as the core solution has a low non-solvent/solvent ratio, the solvent/non-solvent exchange at the dope-core interface is relatively slow; and as the bath has a high non-solvent/solvent ratio, the solvent/non-solvent exchange at the dope-bath interface is relatively fast. This also promotes formation of smaller pores in the skin layer and larger pores in the lumen layer. When the core solution does not contain any non-solvent, there is no initial solvent/non-solvent exchange at the dope-core interface, resulting even larger pores in the lumen layer. As now can be appreciated, the pore sizes in the skin or lumen layer may also be tuned by adjusting the solvent/non-solvent ratio in the bath or the core solution.

An air gap between the spinneret and the bath may have another undesirable effect, in that once precipitation has occurred, the weight of the precipitated fiber portion in the air will pull the higher portion of the fiber near the spinneret which has not fully solidified, thus causing deformation of the pores and the fiber, even breakage if the air gap is too larger.

With no air gap, the above effects can be avoided, and the skin layer may be made nanoporous while the lumen layer is microporous.

A nanoporous layer contains pores that have an average pore size of less than 100 nm, such as less than about 10 nm. The nanopores in a nanoporous skin layer may have an average pore size of less than about 7 nm. A microporous layer contains pores that have an average pore size of larger than 0.1 μm, such as larger than about 0.3 μm. The micropores in a microporous layer may have sizes from about 0.5 μm to about 3 μm. It is possible that there may be some pores larger than 100 nm in a nanoporous layer, but the percentage of such large pores should be very small such that their presence does not significantly affect the performance of the fiber membrane in terms of the substance or materials that may be filtered through the skin layer. Similarly, a microporous layer may have a small percentage of smaller pores as long as the filtering performance is not substantially affected by their presence. For pores with irregular shapes, the average pore sizes may be measured based on the largest size of particles that can be filtered through the pores.

In addition to adjusting the solvent/non-solvent concentrations in the coagulation bath and, optionally, in the lumen-defining fluid, a number of other factors can also affect the pore sizes in the resulting fiber, and these factors should be suitably selected or adjusted to achieve the desired pore sizes and pore size distribution in the resulting fiber. For example, the nature of the polymers, solvent, and non-solvent in the different solutions, the flow rates, the composition or content of the various solutions and the coagulation bath, the temperature of the solutions, the post treatment of the fiber membrane, the dimensions of the extruder, the drawing speeds, or the like, may each have some impact on the pore size or pore side distribution.

However, once the other parameters and factors have been suitably selected, the pore sizes may be controlled mainly by varying the compositions of the fiber-forming solution, the coagulation bath, and optionally, the lumen-defining fluid.

As mentioned, the rate of fluid flows may impact on the pore sizes. The fluid flows may be controlled in any suitable manner known to those skilled in the art. Unless otherwise specified, the flow rates discussed herein refer to flow rates of the fiber-forming solution and lumen-defining fluid through spinneret 102. A flow rate refers to the total amount of a fluid flow flowing through spinneret 102 in a unit time. In a laminar flow, the adjacent fluids although in physical contact may flow at respective flow rates. Some transversal diffusion can occur at the interface region between two adjacent fluids but the general cross-sectional dimension of each flow of fluid can remain substantially constant around exit end 106, so that the extruded fiber will have a substantially uniform diameter and wall thickness.

In some embodiments, suitable flow rates of the fiber-forming solution 114 and lumen-defining fluid 116 may have a ratio of 8:5. For example, the flow rates may be 0.08 ml and 0.05 ml/min, respectively.

Depending on the applications in which the fiber membrane is to be used, the pore sizes and size distribution may be controlled through the techniques discussed herein.

For example, for applications in artificial renal proximal tubules or artificial kidneys, the concentrations of the solvent and non-solvent in the coagulation bath may be selected so that pores in the skin layer of the fiber membrane have an average pore size of less than about 7 nm. As can be appreciated, when the skin layer has pores sized less than about 7 nm, human albumin in the blood, which has a size of about 7 nm, is not likely to pass through the skin layer and enter into the lumen of the fiber membrane from the outer surface. The pores in the skin layer may also be sized to prevent passage of molecules that have molecular weights larger than 60 or 70 kDa. The lumen-defining fluid may be selected to control pore sizes in the lumen layer, such that pores in the lumen layer have an average pore size of about 0.5 to about 3 µm. If the pores in the lumen layer are smaller than about 0.5 µm, transport of some desired substances such as solutes through the fiber membrane may be significantly hindered. When the pore sizes in the lumen layer are larger than about 3 µm, proximal tubular cells may be trapped inside the lumen pores, resulting in clogging of the fiber membrane.

The fiber membrane in flow 120 is fully, or sufficiently, precipitated (solidified) in coagulation bath 110, and is then extracted and wound for further processing and treatment. For example, the precipitated fiber may be washed or rinsed, dried, and rewet. The movement of the fiber in the bath 110 may be guided by rollers, such as rollers 122. The fiber flow 120 may be wound up using a collection wheel (not shown), and may be drawn at a suitable speed. The drawing speed may be selected depending on the particular application and the precipitation time required. For example, a drawing speed of about 0.3 m/min may be suitable in some embodiments. The wound fibers may be immersed in deionized (DI) water for at least 24 hours to remove any residual organic solvent.

As can be understood, a fiber may be continuously produced in a wet spinning process.

The resulting fiber may be cut to desired lengths for further treatment or use. The residual solvents, non-solvents, and a portion of the hydrophilic polymer may be removed before or after cutting, and may be removed through the pores of the fiber membrane or an open lumen. When the lumen-defining fluid is not permeable through the fiber membrane, it may be removed through the open lumen. Conveniently, if the lumen-defining fluid is a coagulation solution formed of the solvent and the non-solvent, it may be removed through the pores, or the lumen, or both the pores and the lumen.

To check or to ensure the pores in the skin layer are within the desired ranges, a solute rejection test may be performed, as can be understood by those skilled in the art. Alternatively, the pore sizes may be measured from images of the samples such as electronic scanning microscopic (SEM) images. It is also possible to determine the pore size by measuring the cut-off molecular weight of the permeates that can pass through the different layers. In particular, the pore sizes in the skin layer control the membrane permeability and the maximum particle size that can pass through the membrane, the smallest pores in the fiber membrane are in the skin layer.

In a particular process, solutions containing substances of different molecular weights (or particle sizes) may be filtered through the fiber membrane. The compositions of the feed and the filtrate are analyzed. If the fiber membrane allows desired substances to pass through but blocks the undesired substances, it can be expected that the pore sizes in the skin layer are within the desired range.

The pore sizes in the lumen layer can be determined from SEM images of the lumen layer.

In an exemplary embodiment of the present invention, a layer of hydrogel may be formed on the lumen layer of the fiber membrane. Conveniently, the micropores in the lumen layer facilitate attachment and formation of the hydrogel layer. Know hydrogel formation and attachment techniques may be used to form the hydrogel layer. Suitable hydrogels may be formed of fibrin, alginate, laminin; or the like. In one embodiment, the hydrogel is formed of fibrin.

In a further exemplary embodiment of the present invention, cells are attached to the lumen layer of the fiber membrane. Cells may be initially attached to the hydrogel that is formed on the lumen layer. The cells may be cultured and allowed to proliferate in the hydrogel and on the lumen surface.

In some embodiments, the hydrogel, such as when made of fibrin, laminin or gelatin, may be biodegradable. Conveniently, the hydrogel when degraded can be removed either though the lumen or through the pores of the fiber membrane, allowing the cells to directly attach to the lumen surface, and to proliferate to form a confluent monolayer of cells on the lumen surface.

The cells may include kidney cells, renal tubule cells, and other cell types. For example, the cells may include human renal proximal tubule epithelial cells (hRPTEC).

The hydrogel for coating the fibers may be selected so that it is suitable for coating on different substrate materials and suitable for coating on porous membranes with curved surfaces. The substrate materials may be fabric, ceramic, plastic, polymer, glass, or the like. Different cross-linkers may be used for different hydrogel coatings. For example, calcium chloride may be used to cross-link alginate in alginate hydrogel, and thrombin may be used to cross-link fibrin in fibrin hydrogel.

In an exemplary embodiment of the present invention, a suitable cross-linker is first deposited on the lumen surface of the hollow fiber membrane, and a solution containing a mixture of a selected cross-linkable hydrogel precursor and selected seed cells is then introduced into the lumen. The cross-linkable precursor is cross-linked with the cross-linker on the lumen surface to form a hydrogel matrix on the lumen surface, with the seed cells trapped inside the hydrogel. The hydrogel may be alginate or fibrin hydrogel. The cross-linker may be calcium chloride. The seed cells may be Madin-Darby canine kidney (MDCK) epithelial cells, or human proximal tubular cells (hPTCs).

The cells dispersed in the hydrogel precursor solution can be conveniently uniformly immobilized onto the lumen surface of the hollow fiber as a thin hydrogel layer is formed on the lumen surface. With a proper culturing environment, the cells will slowly proliferate. The hydrogel matrix can be gradually degraded, to allow a confluent monolayer of cells to attach to lumen surface of the hollow fiber.

With some modification, which will be apparent to those skilled in the art, the coating process may also be applied to hydrogel coating of multiple fibers in a hollow fiber cartridge (see below).

Conveniently, a layer of the hydrogel may be formed on the lumen surface according to the process described herein without filling the entire lumen with the hydrogel. As can be understood, a hydrogel that fills the entire lumen would block or impede fluid flow through the lumen. In some embodiments, the hydrogel layer formed on the lumen surface can be relatively thin, such as in the range of about 10 to about 60 µm. In a particular embodiment, the hydrogel layer may have a thickness of about 30 µm. This arrangement allows fluids to flow through the lumen without blockage and thus facilitates solute exchange between the cells encapsulated in the hydrogel and the fluid passing through the lumen. It is also possible to form a confluent monolayer of the cells on the lumen surface when the hydrogel is degraded over time.

As the hydrogel is used as a carrier to uniformly seed the cells, it may be gradually degraded while the seed cells are cultured and proliferate on the lumen surface. For example, the hydrogel may be bio-degraded by the cells, or chemically degraded at a selected time by introducing a suitable substance into the lumen (for instance, sodium citrate can be used to degrade the alginate hydrogel).

Further, with the seeding process described herein, the cells may be conveniently seeded on the lumen surface uniformly, or substantially uniformly. Relatively inexpensive hydrogels may be used to coat the entire lumen surface, thus facilitating seeding the cells over the entire lumen surface in a relatively short period of time, such as in a few minutes.

This seeding process also does not require a specific extracellular matrix (ECM) coating procedure.

Thus, in exemplary embodiments of the present invention, the fiber membranes may be made suitable for coating a hydrogel together with cells onto the membrane surfaces, particularly the lumen surfaces, as an efficient cell-seeding method. Conveniently, when a hydrogel precursor solution carrying the cells flows through the fiber lumen, the pressure in the solution is azimuthally substantially uniform and a thin hydrogel coating can be substantially uniformly distributed on the entire exposed lumen surface of the hollow fiber. If the cells are initially well dispersed in the hydrogel precursor solution, they will also be uniformly distributed in the coated hydrogel and on the lumen surface. Such a seeding process is convenient and can be completed in a relatively short period, as compared to conventional seeding techniques for seeding cells in artificial renal tubule devices (see Background).

A further embodiment of the present invention relates to an artificial renal proximal tubule which is formed of a tubular fiber membrane. The fiber membrane has a nanoporous skin layer and a microporous lumen layer. The skin layer defines the outer surface of the fiber membrane. The lumen layer defines the lumen and the lumen surface of the fiber membrane. The fiber membrane may be formed according to the method described above, or another method suitably modified from the above method.

As now can be understood, the polymeric materials used to form the tubular fibers should be soluble in a suitable solvent for performing a phase inversion fabrication process. Further, they should provide sufficient mechanical strength to withstand the pressure and shear force the fibers may encounter during normal use of the fibers in the intended applications, and have high chemical stability and heat stability in the normal use conditions. The fibers may also have suitable biocompatibility for use as artificial organs for humans.

In another embodiment, a plurality of fiber membranes may be provided in a cartridge 200, as illustrated in FIG. 2. Cartridge 200 has a generally cylindrical body that defines a middle chamber 202 and two end chambers 204 connected to chamber 202 by fiber mounting sections 206. End chambers 204 are separated and sealed from middle chamber 202 by mounting sections 206. Ends of tubular fiber membranes 208 are mounted on mounting sections 206 such that end chambers 204 are fluidly connected by the lumens of fibers 208 passing through middle chamber 202. Each end chamber 204 includes an input/output port 210, and middle chamber 202 has two input/output ports 212.

Fibers 208 include one or more tubular fiber membranes described above. In one embodiment, all of the fibers 208 in cartridge 200 may be formed as described herein.

Fluid flow control devices (not shown) may be provided to regulate and control fluid flow through cartridge 200.

Proper sealing should be provided to avoid direct fluid communication or leakage between the middle chamber 202 and each of the end chambers 204, as can be understood by those skilled in the art.

Each pair of end chamber 204 and port 110 provides a conduit for fluid communication with one end of the lumens of the fiber membranes 208. Each port 112 provides a conduit for fluid communication with chamber 202. There is limited transportation of mass between chamber 202 and the lumens of fiber membranes 208 through the pores of the fiber walls, as can be understood by those skilled in the art.

In use, a fluid may flow from one end chamber 204 to the other end chamber 204 through the lumens of fibers 208, and another fluid may flow through middle chamber 202. Depending on the particular application, small components in one of the fluids with sufficiently small sizes can pass through the pores in the walls of fibers 208 and enter into the flow of the other fluid. Larger components in each fluid will remain in the respective fluid in cartridge 200.

The use and operation of cartridge 200 will be readily understood by those skilled in the art. For example, cartridge 200 can be conveniently used to provide increased fluid throughput, as compared with a single fiber.

When the pores on the inner surface of the fiber membrane are sized to enhance the adhesion of coated cell/hydrogel/ECM onto the hollow fiber membrane, the following factors may need to be considered in the selection of the pore size on the lumen surface.

Figure 3A:
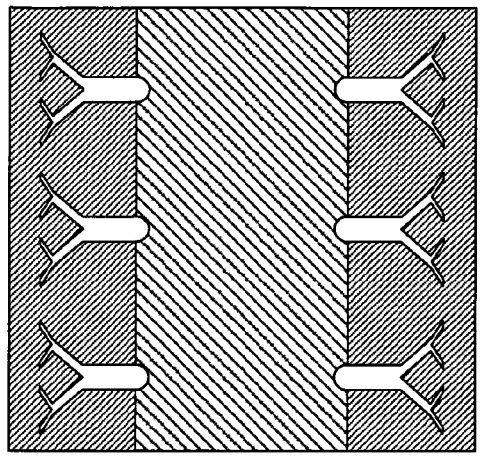
FIGS. 3A, 3B, 3C, and 3D are schematic cross-sectional views of possible fiber structures, exemplary of embodiments of the present invention.
Figure 3B:
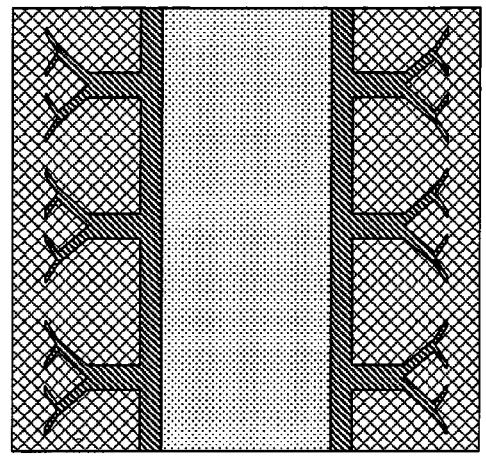

Deep and large pore structures, as illustrated in FIGS. 3A and 3B, may assist binding between the coated hydrogel matrix and the membrane. As illustrated in FIG. 3A, large pores (white space) are formed around lumen surface, which have branched structures with smaller pores at the terminal ends of the larger pores and deeper into the fiber wall. This type of pore structure may be useful for coating an alginate hydrogel. The hydrogel can penetrate into the smaller pores through the larger pores, as illustrated in FIG. 3B (densely hatched area). When the hydrogel contracts, the hydrogel branches penetrated into the smaller pores can hold the coated hydrogel layer tightly to the lumen surface.

Figure 3C:
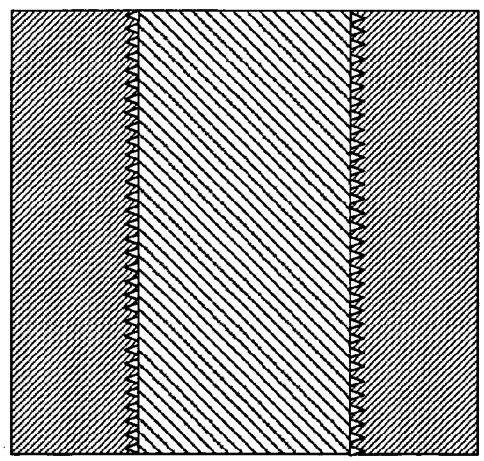
Figure 3D:
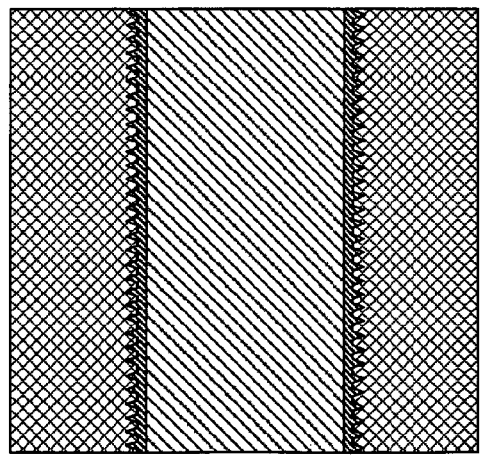
Figure 5A:
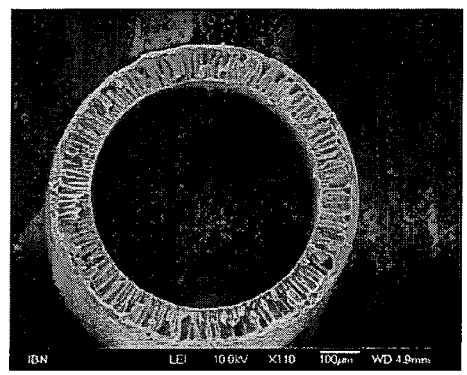
FIGS. 5A, 5B, 5C, and 5D are SEM images of a comparison hollow fiber.
Figure 5B:
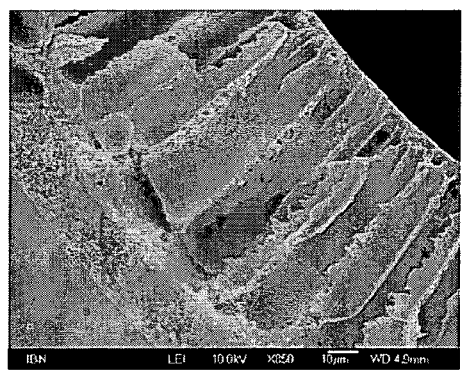

When the coating matrix has a high water content (or, the coating solution is dilute), the hydrogel layer is typically thin after dehydration, and it is typically difficult for this type of hydrogel layer to cover large pores. Thus, for such a coating matrix, a lumen surface with small orifices, as illustrated in FIG. 3C may be appropriate. For example, this may be the case when laminin is used as the hydrogel. As illustrated in FIG. 3D, when the lumen layer has smaller and shallower pore structures as illustrated in FIG. 3C, a thinner hydrogel layer may be formed on the lumen surface.

Generally, the cells/bacteria/particles encapsulated in a coating matrix should be larger than the surface pores so that they are prevented from entering into the pores and be trapped therein. Of course, there are exceptions to this general guideline. For example, this guideline does not apply if it is intended that the cells/bacteria are to be immobilized in the pores, such as in some membrane bio-reactors.

The mechanical strength of the fiber is dependent on the porosity of the fiber. When the size of the hollow fiber is increased, sufficient mechanical strength of the fiber may be maintained even if the sizes of the pores on the lumen surface are also relatively increased.

Tuning the pore sizes on the lumen surface allows the fibers to be formed to suit different applications, different coating materials, and different cells/bacteria types that are to be encapsulated inside. Thus, the fiber membranes disclosed herein are easily adaptable and may find applications in different fields, such as in the fields of artificial organs, membrane bioreactors, and membrane biosensors.

Representative cross-sectional SEM images of exemplary hollow fiber membrane are shown in the figures, such as FIGS. 4A, 4B, 4C, and 4D, as explained in the Examples. As can be seen from these figures, such as in FIGS. 4A, 4B, 4C, and 4D, the sample fiber membrane has a porous tubular body defining a lumen. The skin layer in the tubular body is nanoporous. The pores in the skin layer are sufficiently small to prevent capillary blood (proteins and healthy cells) flow through the skin layer into the tubular body and thereafter the lumen space. The average pore size of the pores in the skin layer is less than about 7 nm. The lumen layer is microporous, and the inner (lumen) surface of the tubular body has larger pore openings that are suitable to facilitate hydrogel/cell attachment. As can be seen, the tubular body has large finger-shaped voids (macrovoids) extending between the skin layer and the lumen surface.

As these macrovoids can significantly affect the mechanical strength of the fiber, the presence of large macrovoids may not be desirable in some applications. As discussed elsewhere, to reduce or limit formation of the macrovoids, a number of measures may be taken in the manufacturing process.

As now can be appreciated, some modifications to the embodiments described above are possible.

Exemplary embodiments of the fiber membranes described herein have tunable dimensions and can have a mechanical strength that is suitable for use in artificial kidneys or artificial renal proximal tubules. The dimensions of the fibers may be conveniently adjusted by controlling flow rates of the feed solutions during the fabrication process. Kidney cells may cultured inside the lumen, exemplary of an embodiment of the present invention.

As the inner (lumen) surface of the fiber is coarse and porous, a suitable hydrogel can be conveniently attached to the lumen surface, and kidney cells may be cultured in or on the hydrogel. The hydrogel may be biodegradable so that when the hydrogel is biodegraded, the kidney cells can attach to and proliferate on the lumen surface.

The porous inner surface of the fiber can facilitate tight binding with a coated hydrogel layer. Kidney cells encapsulated in the hydrogel matrices could proliferate on the fiber membrane when the hydrogel is degraded and gradually removed, and eventually a monolayer of epithelial cells can form on the inner fiber surface. The confluent cell layer on the lumen surface may exhibit the same polarization as in a natural kidney—with the microvilli facing the fiber lumen.

The cell-layered hollow fibers may be assembled into cartridges (see e.g. FIG. 2), and be used for reabsorbing useful substances in the glomerular filtrate back to human blood in a bioartificial kidney device.

As the outer (exterior) surface of the fiber is smooth and dense, the skin layer at the outer surface of the fiber conveniently provides immunoprotection for the cells from the attack of antibodies in the blood, and prevents serum albumin and other large molecules from leaking into the urine through any gaps in the cell layer.

The structure of the fiber membrane can also conveniently reduce protein adsorption by the fiber wall, as compared to the conventional fibers with a skin layer at the inner surface.

The dimensions of the fibers for different applications may be selected based on various factors and properties of the fiber, including the pressure drop and flow rate in the tubules, the response of cells to shear stress, mechanical strength, and the like.

The hollow fiber membranes should be made to be able to withstand the pressure that will be applied during normal use of the fiber in the desired application. It is expected that there is a linear relationship between the Young's modulus of elasticity and the collapse pressure of a thin-walled hollow fiber membrane. This relationship may be utilized to select the suitable material and dimension of the fiber for a given application.

The fibers described herein are suitable for use as reabsorption fibers, as compared to hemodialysis fibers. It may be desirable in some applications that the reabsorption fiber is able to prevent antibodies (e.g. immunoglobulin A, D, E, G and M, with a molecular weight of no less than 150 kDa) from attacking kidney cells attached to lumen wall in the fiber.

It may also be desirable that in an artificial renal proximal tubule the renal tubule cells form a confluent cell layer, which may be a monolayer, on the lumen surface of the fiber membrane. If the cell layer on the lumen surface has gaps, blood cells and proteins in the extra-capillary space surrounding the fiber may leak into the fiber lumen through the gaps in the cell layer during reabsorption, and appear in the urine. Thus, it may be desirable that the fiber walls block transport of serum albumin (60 kDa) through the walls.

In a reabsorption process, the outer surface of the reabsorption fiber would face the blood and the inner surface of the reabsorption fiber would face the cell layer. Since the skin layer is adjacent the outer surface, the large molecules (for example, albumin) could not penetrate the fiber wall and could only be carried away by the blood flowing outside the fiber.

Conveniently, the dense, nanoporous skin layer can prevent entry of undesired substances in the blood flowing outside the artificial renal tubule; and the microporous lumen layer can enhance the attachment of ECM and cells and allow a confluent cell layer to be, formed thereon.

In contrast, with a conventional hemofiltration fiber membrane that has large pores near the outer surface and small pores near the lumen surface, large molecules from the blood (e.g. albumin and antibodies) can enter the fiber wall from the large pores on the outer surface and be trapped inside the small pores near the inner surface, resulting in membrane clogging and permeability loss.

Further, there is less trans-membrane pressure in a reabsorption process, as compared to a hemodialysis process, the required mechanical strength of a reabsorption fiber may be lower than that for a hemodialysis fiber.

Fibrin has been shown to promote differentiation of renal proximal tubule cells into confluent cell monolayer along the lumen surface when it is coated on the lumen surface. As fibrin is an inexpensive material, it may be used to cover the entire lumen surface at a relatively low cost.

The exemplary hollow fiber membrane described herein can thus reduce membrane clogging and improve cell-matrix attachment on the luminal surface.

Exemplary embodiments of the present invention are further illustrated with the following examples, which are not intended to be limiting.

EXAMPLES

Example IA

Preparation of Sample Hollow Fiber Membranes with Oil

Polyethersulfone (PES, average molecular weight (MW)=51 kDa, BASF™) and polyvinylpyrrolidone (PVP, average MW=25 kDa, Merck™) were slowly added to N-methyl-2-pyrrolidone (NMP) in a glass bottle. The concentrations of PES, PVP, and NMP for different samples are listed in Table I. The mixture was stirred until a homogeneous solution (referred to as the dope solution) was obtained. The dope solution was used to in an extrusion process to form the tubular fiber body, as further described below.

TABLE I

Contents of Dope Solution (wt %) for Different Fiber Samples

| Sample | PES | PVP | NMP |
|---|---|---|---|
| S1 | 18 | 8 | 74 |
| S2 | 18 | 10 | 72 |
| S3 | 16 | 10 | 74 |
| S4 | 20 | 8 | 72 |

A core solution was prepared using a biocompatible oil, FC3283 (3M™). FC3283 oil is immiscible with water and NMP, and has a density of 1820 kg/m$^3$ and a viscosity of 1.4 cp. The core solution was used in the extrusion process to occupy the lumen space, as further described below.

The extrusion procedure was as described above and illustrated in FIGS. 1A, 1B, and 1C. The dope and core solutions as prepared above were pumped into the extruder at flow rates of 0.08 and 0.05 ml/min, respectively. The feed solutions were injected into the extruder to form a coaxial laminar flow, with the core solution as the central (inner) layer of the flow and the dope solution as the peripheral (outer) layer.

The exit of the extruder was immersed in a coagulation bath composed of 10 vol % NMP in water (H$_2$O) at room temperature. The outer layer of the laminar flow (substantially composed of the dope solution) was solidified in the bath to form a tubular fiber body. The core solution remained as a fluid so that a core (lumen) was formed in the tubular fiber.

Small adjustments of the dimensions of the fiber (inner and outer diameters and layer thickness) were controlled by controlling the volume ratio of the injected core and dope solutions, such as by adjusting their respective injection flow rates.

The resulting hollow fibers were guided by rollers, and wound up by a collection wheel at a speed of 0.3 m/min. Next, the fibers were immersed in deionized (DI) water for at least 24 hours to remove residual organic solvent. They were cut into segments of a desired length, and flushed with sufficient DI water to remove the FC3283 oil in the fiber lumen.

One set of samples was freeze-dried and characterized by SEM.

Another set of samples was immersed in a 35 wt % glycerol aqueous solution for 1 day before drying at 70° C. for 24 h. These fibers were then assembled into cartridges for testing solute-rejection properties. This set of sample fibers was next rinsed extensively, and autoclaved at 120° C. for 30 min for hydrogel coating and cell culture.

Using extruders of different dimensions, sample hollow fibers with three different dimensions were fabricated. Specifically, one group of sample fibers had an outer diameter of about 1550 μm, lumen diameter of about 1050 μm, and wall thickness of about 250 μm; another group of sample fibers had an outer diameter of about 780 μm, lumen diameter of about 490 μm, and wall thickness of about 145 μm; and a further group of sample fibers had an outer diameter of about 330 μm, lumen diameter of about 240 μm, and wall thickness of about 45 μm.

Further tests described below were performed on the sample fibers with the outer diameter of about 780 μm.

FIGS. 4A, 4B, 4C and 4D show scanning electron microscopic (SEM) images of a sample tubular fiber membrane (S2 in Table I). As can be seen, the sample hollow fiber had a uniform wall thickness. Finger-like macrovoids were present in the fiber between the skin layer and the lumen layer, which extended generally radially. The largest voids appeared near the lumen surface, but were not open to the lumen. The skin layer near the outer surface had smaller pores, with sizes below about 10 nm. The skin layer was thus sponge-like.

Figure 4A:
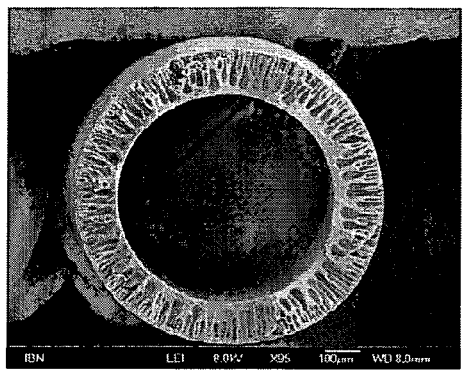
FIGS. 4A, 4B, 4C, and 4D are scanning electronic microscopic (SEM) images of a sample tubular fiber membrane, exemplary of an embodiment of the present invention.
Figure 4B:
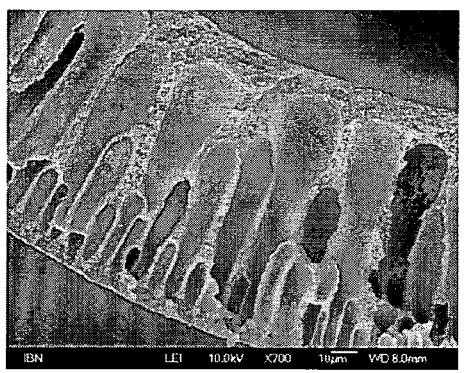
Figure 4C:
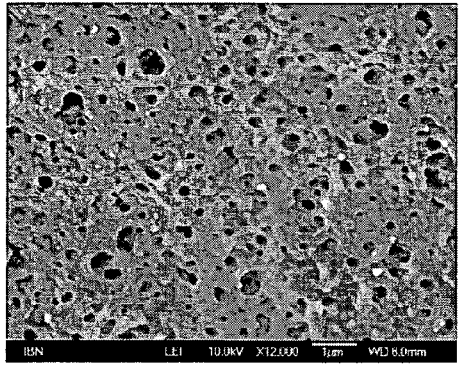
Figure 5C:
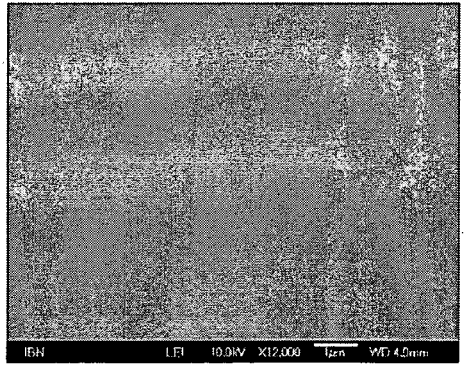

As can be observed from FIG. 4C, the lumen surface of the sample fiber was not smooth, and there were many large pores, with pore sizes up to 0.5 μm. These large pores formed a three-dimensional porous network in the lumen layer.

Figure 4D:
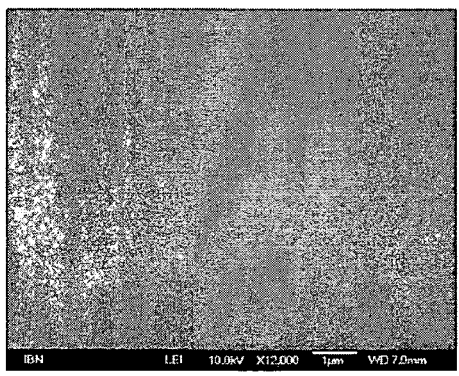
Figure 5D:
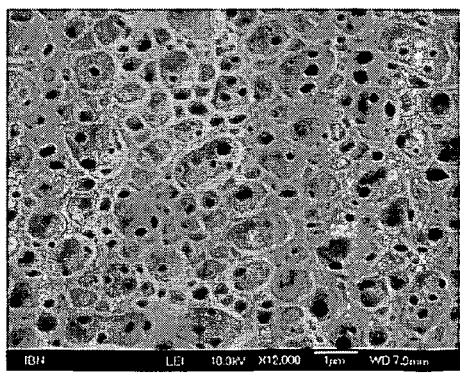

In comparison, the outer surface appeared rather dense (see FIG. 4D). It was found that nanometer-sized pores were present in the skin layer (from images of very high magnification, which are not shown).

The pore sizes of the pores in the skin layer limited the maximum size (or maximum MW) of solutes that could pass through the membrane from the outside through the outer surface.

The formation of finger-like macrovoids could be undesirable in some applications, because the fiber wall near the ends of the macrovoids might be defect-prone due to reduced strength.

It was found that more sponge-like porous structure could be obtained by increasing either the polymer concentration in the dope solution or the viscosity of the dope solution. For example, by increasing the PES concentration in the dope solution from 18 to 24 wt %, the volume of the macrovoids was significantly reduced.

Based on the experimental data, it is expected that a macrovoid-free fiber can be obtained by further increasing the PES concentration in the dope solution.

The sample fibers in Example IA are considered to be suitable for reabsorption and for use as artificial renal proximal tubules, due to their pore size distribution.

The tested sample fiber was found to have a Young's modulus of about 117 MPa. It is expected that such a fiber would have sufficient mechanical strength for reabsorption applications.

Without being limited to a particular theory, a reason for the above expectation is that it has been reported in the literature a small osmotic pressure differential of two to three mOsm/kg H$_2$O was adequate to promote large isosmotic fluid transport in renal proximal tubule, due to the very high diffusive water permeability of the renal proximal tubule cells. As a result, the pressures on the tube side and the shell side in a reported renal tubule assist devices were 5-10 mmHg and 10-25 mmHg, respectively. Thus, the pressure difference across the reabsorption fiber could be much less than that in a typical filtration fiber, which is typically about 100 mmHg. Therefore, the mechanical strength required in a reabsorption fiber is likely significantly less than in a filtration fiber. It has been reported that for a filtration fiber, a Young's modulus of about 160 MPa was adequate. Thus, the sample fibers tested are expected to have sufficient mechanical strength for reabsorption applications.

Example IB

Sample Filtration Fiber Membrane (Comparison)

For comparison purposes, sample filtration fibers were fabricated using a conventional dry-wet-spinning process, with the same extruder as used in Example IA. The dope solution and the coagulation bath were prepared and the extrusion procedure was performed similarly as described in Example IA, with the changes noted below. In particular, the dope solution had 18 wt % of PES and 10 wt % of PVP in NMP. The dope solution was injected into the extruder at a flow rate of 0.2 ml/min was used. The core solution was formed of 10 vol % of NMP in water, and was injected into the extruder at a flow rate of 0.3 ml/min. The extruder exit was placed 10 mm above the primary coagulation bath.

FIGS. 5A, 5B, 5C and 5D show SEM images of a comparison filtration fiber membrane made according to the above procedure.

As compared to the sample fibers in Example IA, the sample fibers of Example IB had a different pore structure and pore size distribution. In particular, finger-like macrovoids were present between the lumen and outer surfaces of the fibers of Example IB, with larger voids near the outer surface, and the small branches pointed to the lumen surface (see FIG. 5B). More importantly, the lumen surface was very smooth (the lumen layer had nanometer-sized pores), while the skin layer had large, micrometer-sized pores.

Example II

Preparation of Sample Hollow Fiber Membranes with Water/NMP Mixture as Core Solution Sample fiber membranes were prepared according to the procedure of Example I, except that the core solution was a mixture of water and NMP.

An advantage of using $H_2O$/NMP mixture of the core solution is that after the fiber membrane was formed, the core solution may be conveniently removed from the lumen through the membrane pores, such as by diffusion. In comparison, when oil is used as the core solution, the oil in the lumen was flushed out with water after the fiber membrane had been formed, as oil was immiscible with water or NMP.

Another advantage of using $H_2O$/NMP mixture as the core solution is that the pore sizes on the inner surface of the fiber membrane can be conveniently tuned by varying the volume fraction of NMP in the core solution.

Test samples were formed with various NMP concentrations in the core solutions. The NMP concentration was varied from about 60 v % to 90 v %. The sizes of the pore openings on the inner surface of the fiber membranes increased with increasing concentration of NMP. Representative SEM images of the sample fibers are shown in FIGS. 6A, 6B, 6C, and 6D, with the NMP concentration in the core solution being 90 v % (FIG. 6A), 80 v % (FIG. 6B), 70 v % (FIG. 6C), and 60 v % (FIG. 6D). The coagulation bath had 10% of NMP/water for the samples shown in FIGS. 6A, 6B, 6C, and 6D. At [NMP]=90 v %, the pore openings were about 10 μm in diameter. At [NMP]=60 v %, the pore openings were about 0.1 μm in diameter.

Further representative test results are shown in FIGS. 7A, 7B, 7C, and 7D, with the NMP concentration in the core solution being 90 v % (FIG. 7A), 80 v % (FIG. 7B), 70 v % (FIG. 7C), and 60 v % (FIG. 7D). The coagulation bath had 50% of NMP/water for the samples of FIGS. 7A, 7B, 7C, and 7D.

Example III

Solute Rejection Tests

A cartridge containing 15 fibers of 110 mm in length was used to test for solute rejection properties. It was thoroughly flushed with DI water to remove residual glycerol before the test. A continuously stirred aqueous solution composed of 9.14 g/L of blood serum albumin, 0.19 g/L of urea and 0.007 g/L of creatinine was used as the feed, which was pumped into the cartridge at a preset rate. The solution flowed through the extra-capillary space of the cartridge, during which part of the water and small molecules passed through the membrane to form the filtrate. The filtrate was sampled, and its flow rate was monitored. Fluid pressures before and after the cartridge were measured by pressure sensors (40PC015G, Honeywell, Singapore). The concentrations of both the feed and the filtrate were analyzed by a Cobas™ C 111 Analyzer (Roche, Switzerland).

Table II shows representative results of solute rejection tests of sample hollow fibers fabricated at various dope compositions (see Table I). The feed was an aqueous solution of albumin (9.14 g/L), urea (0.19 g/L) and creatinine (0.007 g/L). The solute rejection tests were conducted at a transmembrane pressure (TMP) of 2 psi (103.4 mmHg). Three solutes, albumin, urea, and creatinine, were used in the tests which were four hours in duration. Urea (60 Da) and creatinine (113 Da) were used as representative small molecules. The sieving coefficient was defined as the ratio of solute concentration in the filtrate to that in the feed. $Q_b$ and $Q_f$ were the flow rates of the feed and filtrate, respectively.

TABLE II

| | | | Sieve Coefficient | | |
| --- | --- | --- | --- | --- | --- |
| Sample | $Q_b$ (ml/min) | $Q_f$ (ml/min) | ALB | Urea | Creatinine |
| S1 | 12.0 | 0.40 | 0.025 ± 0.004 | 0.910 ± 0.007 | 0.971 ± 0.041 |
| S2 | 14.5 | 0.34 | 0.006 ± 0.003 | 0.882 ± 0.001 | 0.920 ± 0.010 |
| S3 | 20.0 | 0.53 | 0.023 ± 0.015 | 0.957 ± 0.012 | 1.018 ± 0.039 |
| S4 | 20.0 | 0.29 | 0.004 ± 0.002 | 0.899 ± 0.003 | 0.995 ± 0.030 |

The test results shown that an increase in either PES or PVP concentration in the dope solution resulted in reduced sieving coefficient of albumin. With a dope solution of 20 wt % PES and 8 wt % PVP in NMP, the albumin concentration was reduced to only 0.4% of that in the feed, indicating that the fiber effectively blocked the crossing of albumin through the fiber wall. In contrast, the sieving coefficients for urea and creatinine were high in all of the fibers tested, showing that the fibers offered a high permeability for small molecules. At the same TMP and membrane surface area, a higher PES or PVP concentration in the dope solution corresponded to a lower filtrate flow rate.

Example IV

Fiber Cartridge

Six sample cartridges, as schematically illustrated in FIG. 2, were prepared, where each sample cartridge contained 10 fibers (S4 in Table I). For a first set of three of the six cartridges, a fluid was fed from the lumen side (intra-capillary space) via the porous lumen surface of each fiber. For a second set of three other cartridges, a fluid is fed from the outside (extra-capillary space) via the skin layer.

Figure 8:
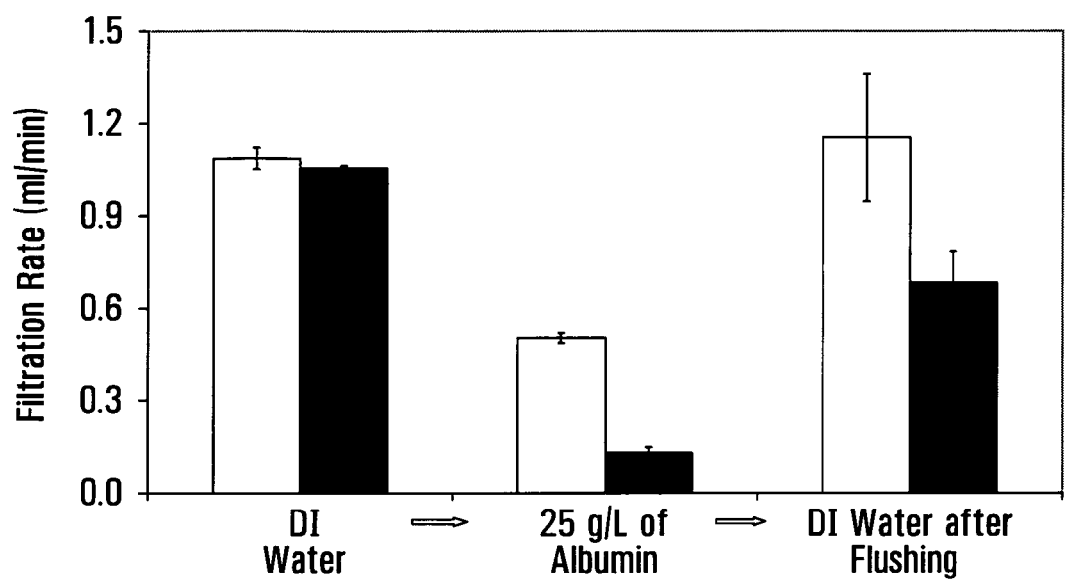
FIG. 8 is a bar graph showing the filtration rates measured from different sample fibers.

DI water was first fed, followed by 25 g/L of albumin solution, and then DI water again after flushing the membrane extensively. All the tests were conducted at a TMP of 2 psi for 1 hour. FIG. 8 shows the test results. The hollow bars represent the filtration rates measured when the feed solution was introduced to the skin layer side and the solid bars represent rates measured when the feed solution was on the lumen side. As shown, the filtration rates were quite similar when DI water was first fed, regardless of whether it was fed from the skin side or the lumen side. This indicated that the transport resistance for the two sets of cartridges was similar. When the albumin solution was fed, filtration rates were reduced for both sets, but especially for the set fed from the lumen side, due to the additional resistance caused by membrane clogging. After the membranes were extensively flushed, the original filtration rate was restored when DI water was fed again from the skin layer. A substantial loss in filtration rate was observed when DI water was fed again from the lumen side, due to irreversible clogging of the membrane by albumin fed earlier from the lumen layer.

Another sample cartridge containing 35 fibers was also prepared, and used to measure protein uptake on the different sides of the fiber membrane, after filtering a 25 g/L albumin solution for one hour through the cartridge. The amount of albumin taken up by the fiber membrane was less than 1% when the feed was fed by contacting the skin layer, and as high as 9% when fed by contacting the lumen surface. In the former case, the albumin formed a thin filtration cake on the outer surface of the fiber, which resulted in some resistance in filtering the albumin solution. After the albumin deposited on the outer surface was flushed away, the filtration rate of DI water was fully recovered. In contrast, had albumin entered into the fiber wall, it would be difficult to flush away the deposited albumin to fully recover the membrane permeability.

Example V

Coating Fiber with Alginate Hydrogel and Kidney Cells

Sample hollow fibers as prepared in Example IA were soaked in sterilized 200 mM $CaCl_2$ solution for 24 hours. The sample fibers were then dried in an oven at 45° C. for 3 hours. Upon water evaporation, $CaCl_2$ salt was deposited on both lumen and outer surfaces of the fibers, and in the small pores within the fiber wall. Separately, sodium alginate was dissolved in Dulbecco's modified Eagle's medium (DMEM) (glucose concentration=1000 mg/dL) under continuous stirring to form a 2.5 wt % solution. The solution was then sterilized using a 0.4-μm filter. Madin-Darby canine kidney (MDCK) epithelial cells were dispersed uniformly in the sodium, alginate solution at $10^6$ cells/ml. The mixture was injected through a needle into the lumen of the hollow fibers. Due to the $CaCl_2$ coated on the fiber wall, the sodium alginate near the lumen surface was cross-linked into a very thin alginate hydrogel layer (typical thickness about 30 μm) within which cells were uniformly immobilized. The coating time ranged from 3 to 5 s, depending on the layer thickness desired. The unbounded hydrogel was flushed out of the fiber with sterilized air.

Example VI

Cell Culture and Characterization

The cell-coated fibers in Example V were immediately preserved in DMEM supplemented with 10% fetal bovine serum (FBS) (GIBCO) and 1% antibiotic-antimycotic (GIBCO), and cultured under a humidified atmosphere of 5% $CO_2$ at 37° C. After 5 to 7 days of culture, sodium citrate was added to the cell culture medium at a final concentration of 1 mM to gradually degrade the alginate hydrogel within the hollow fibers. The cell-coated hollow fibers were characterized after 14 days of culture. They were first fixed in 2% glutaraldehyde in culture medium, and then dried in ethanolic solution with increasing concentrations (35%, 50%, 70%, 80%, 95%, 100% and 100%) for 60 min each. The samples were next dried in an Autosamdri 825 critical point dryer before SEM studies. The dried samples were cut at an angle of about 45° from the fiber axis, such that part of the inner surface was exposed for SEM characterization.

Figure 11A:
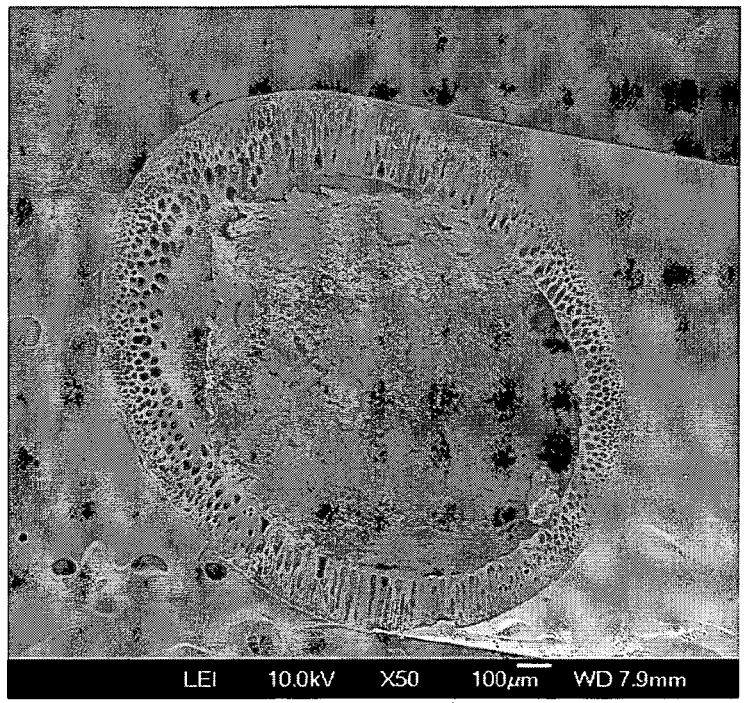
FIGS. 11A and 11B are SEM images of a sample fiber, coated with a confluent monolayer of cells, exemplary of an embodiment of the present invention.
Figure 11B:
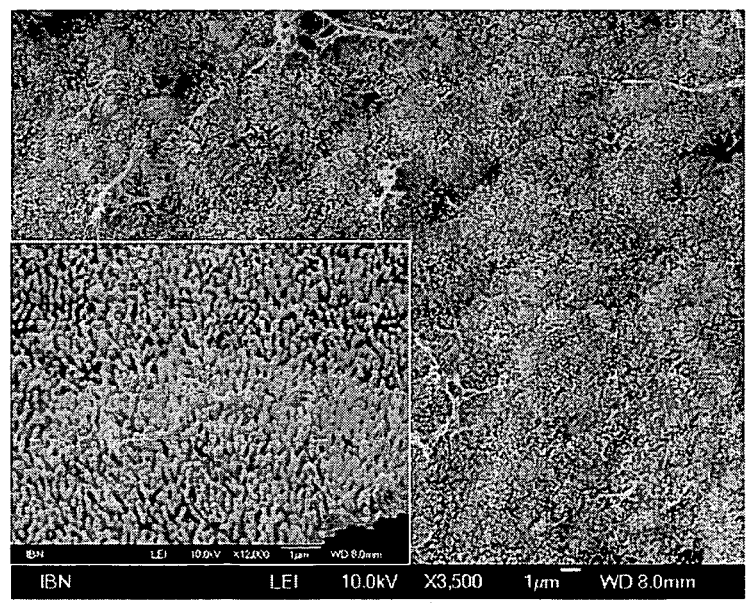

Electron microscopy images of the inner surface of the sample PES reabsorption fibers revealed that a confluent RPTEC monolayer was formed on the lumen surface. See FIG. 11A, which shows an SEM image of a sample fiber where the lumen layer was coated with a confluent monolayer of epithelial cells, taken two weeks after initial cell seeding. FIG. 11B shows an SEM image of the microvilli on the lumen surface of the epithelial cells. Except for artifacts (e.g. voids left by cell detachment in the sample preparation process), the cells covered the entire inner surface of the hollow fiber and demonstrated the correct polarization with many closely-spaced microvilli facing the lumen. The dense microvilli present could significantly increase the surface area of cells, which would be helpful for reabsorbing useful substances from the filtrate (in the lumen), and provide them back into the blood that is flowing outside the hollow fiber. No microvilli were observed on the cells from the side of the cell in contact with the fiber wall, which confirmed that the cell Polarization is suitable for reabsorption application.

Example VII

Coating Membrane Surface with Hydrogel and Seeding Cells

Madin-Darby canine kidney (MDCK) epithelial cells were seeded on the inner (lumen) surface of a sample PES/PVP hollow fiber membrane, and on the outer surface of a polysulfone (PS) (Fresennius™) hollow fiber membrane (for comparison purposes), through a hydrogel. Alginate was selected as the cell-carrying hydrogel and calcium chloride was used as the cross-linker.

Sodium alginic acid in a powder form was dissolved in 1×PBS at a concentration of 2.5 wt %, while calcium chloride ($CaCl_2$) was dissolved in DI water at a concentrations of 100 mM. Solution sterilization was achieved by an autoclave at 121° C. for 20 min. Before mixing with MDCK cells, the alginate solution was filtered using a 0.4-μm-pore-size filter to remove yellow precipitates formed over time.

Both the PES and PS hollow fiber membranes were cut into suitable lengths, sterilized by autoclave, and dried in fume hood.

The inner surface of the PES hollow fiber membrane and outer surface of the PS hollow fiber membrane were completely wetted with the calcium chloride solution. The sterilized hollow fiber membranes were soaked in the calcium chloride solution overnight, and then taken out and dried in a vacuum oven. After drying, calcium chloride was deposited on the selected surfaces of the tested membrane.

A selected amount of the cell-loaded alginic acid solution was injected into and flushed through the lumen of PES hollow fiber membranes, using a syringe with a blunt-tip needle. A layer of the cross-linked and cell-trapped alginate hydrogel was formed on the inner surface of the membrane. The cell-seeded PES hollow fiber membrane was then soaked in a cell culture medium (DMEM) for cell culture.

The PS hollow fiber membrane with deposited calcium chloride was dipped into the cell-loaded alginic acid solution for a short period of time. A layer of crosslinked alginate hydrogel was formed on the outer surface of the fiber membrane with MDCK cells trapped inside the hydrogel. The cell-seeded hollow fiber membrane was soaked in cell culture medium (DMEM) for cell culture.

The cells seeded on the surfaces of the hollow fiber membrane were cultivated in DMEM in an incubator at a temperature of 37° C. and a $CO_2$ concentration of 5%. The cell culture medium was partially replaced by fresh medium every two days.

Figure 9A:
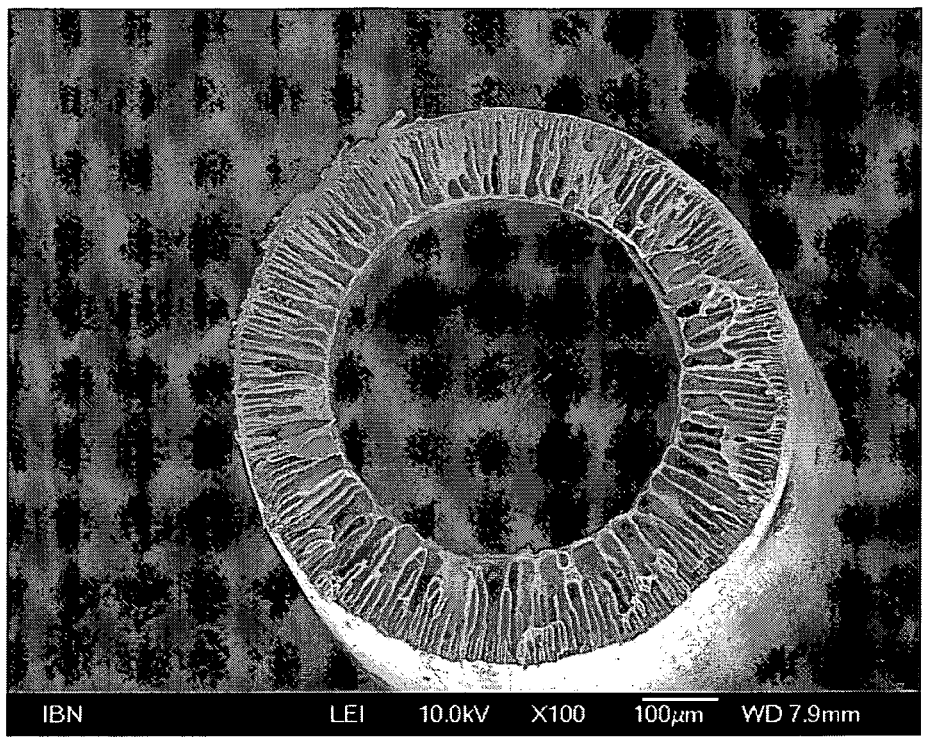
FIGS. 9A and 9B are SEM images of a sample fiber coated with a hydrogel, exemplary of an embodiment of the present invention.
Figure 9B:
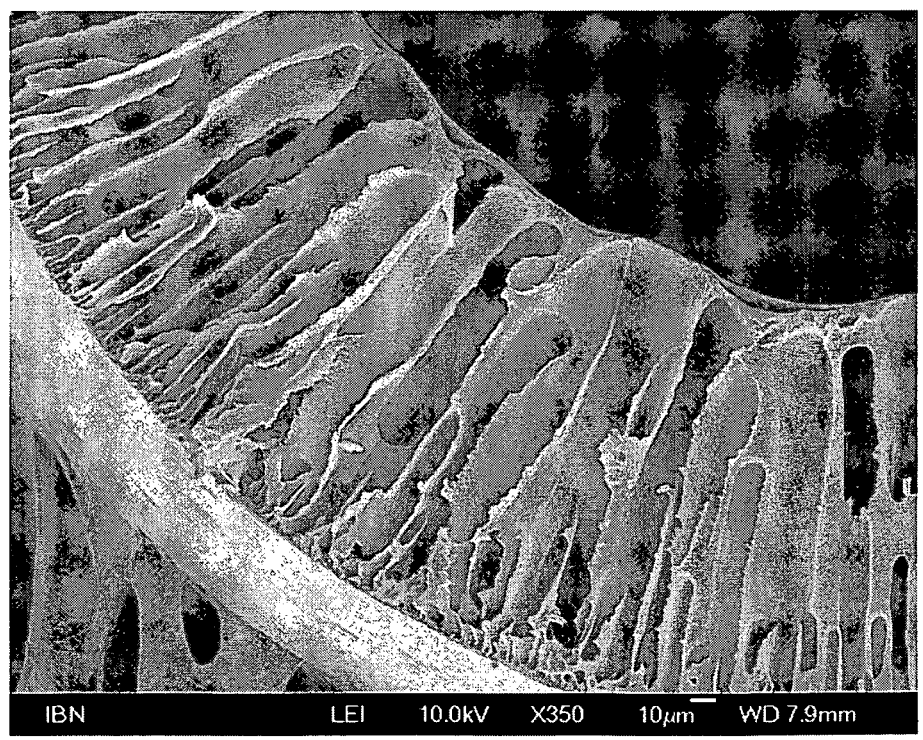

FIGS. 9A and 9B show SEM images of a sample reabsorption fiber coated with an alginate hydrogel.

Figure 10A:
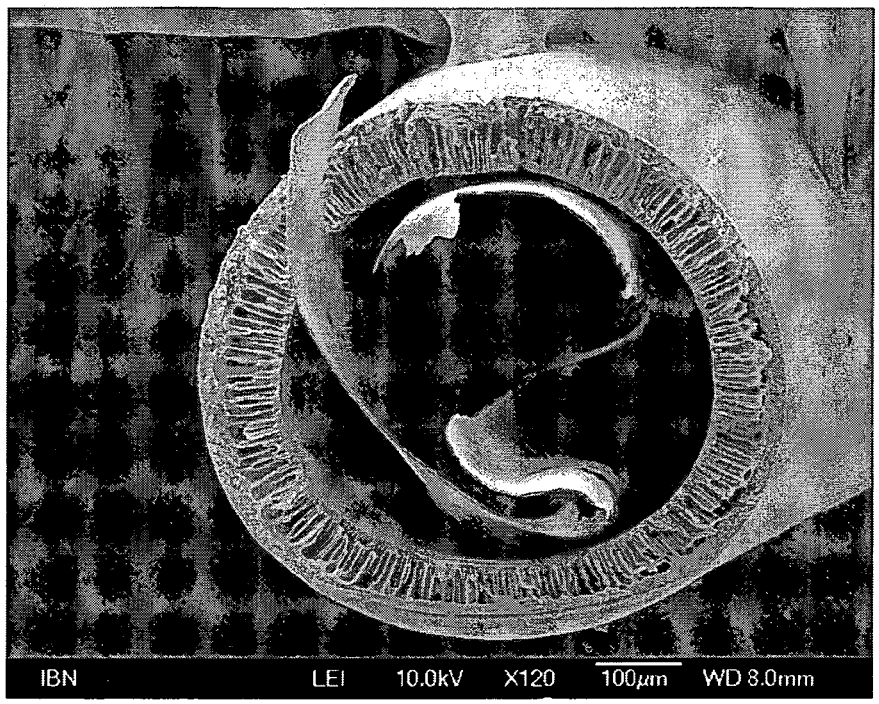
FIGS. 10A and 10B are SEM images of a comparison fiber.
Figure 10B:
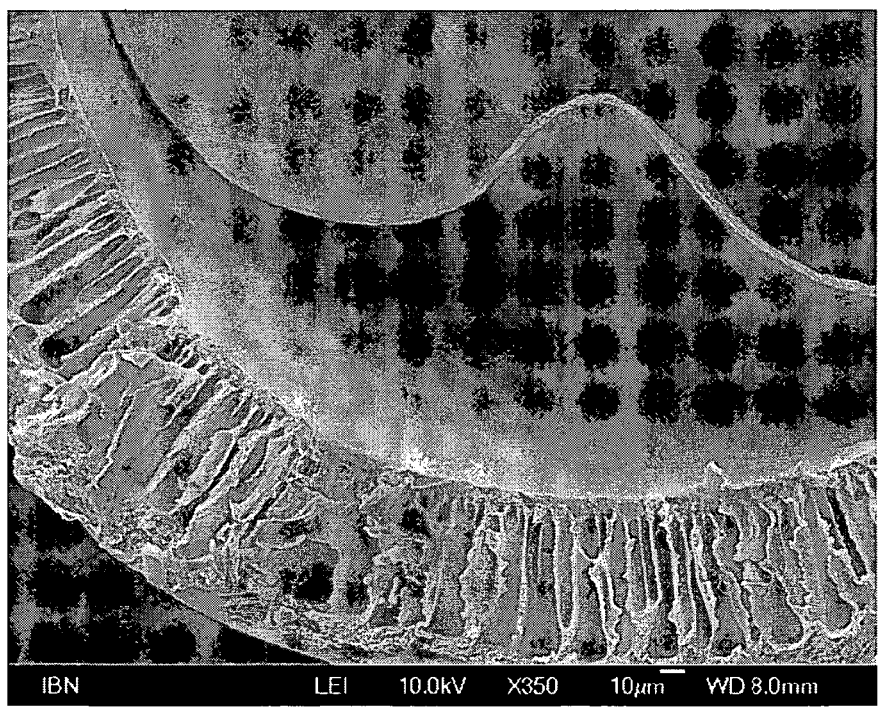

FIGS. 10A and 10B show SEM images of a comparison filtration fiber, which was initially coated with an alginate hydrogel, after dehydration in air. As can be seen, the hydrogel layer was detached from the fiber after dehydration.

Example VIII

Coating Fiber with Fibrin Hydrogel and Cells

Human renal proximal tubule epithelial cells (RPTEC) were seeded and cultured in the lumen of a single sample hollow fiber (S2) coated with 5 mg/ml fibrinogen and 50 U/ml thrombin using a syringe pump perfusion system.

The SEM images (not shown) of the immunostained fibers indicated that a confluent cell monolayer was formed along the lumen surface of the fibrin-coated sample fibers.

Comparison tests were also conducted on fibers without fibrin-coating. It was observed that very few cells attached to the inner surface of the comparison fibers, as compared to the fibrin-coated sample fibers.

When a list of items is given herein with an "or" before the last item, any of the listed items or any suitable combination of the listed items may be selected and used. For any list of possible elements or features provided in this specification, any sublist falling within a given list is also intended. Similarly, for any range provided, any subrange falling within a given range is also intended.

Of course, the above described embodiments are intended to be illustrative only and in no way limiting. The described embodiments are susceptible to many modifications of form, arrangement of parts, details and order of operation. The invention, rather, is intended to encompass all such modification within its scope, as defined by the claims.

What is claimed is:

1. An artificial renal proximal tubule, comprising:
a tubular fiber membrane defining a lumen, said fiber membrane comprising a nanoporous skin layer and a microporous lumen layer, said skin layer defining an outer surface of said fiber membrane and said lumen layer defining a lumen surface of said fiber membrane, wherein pores in said skin layer have an average pore size of less than about 7 nm, and pores in said lumen layer have an average pore size of from about 0.5 to about 3 μm.

2. The artificial renal proximal tubule of claim 1, wherein said fiber membrane comprises polyethersulfone (PES).

3. The artificial renal proximal tubule of claim 1, comprising a layer of hydrogel formed on said lumen layer.

4. The artificial renal proximal tubule of claim 3, wherein said hydrogel comprises fibrin.

5. The artificial renal proximal tubule of claim 1, comprising cells attached to said lumen layer.

6. A cartridge comprising:
a body defining a fluid chamber;
a plurality of tubules including a tubule that further includes a tubular fiber membrane defining a lumen, said fiber membrane comprising a nanoporous skin layer and a microporous lumen layer, said skin layer defining an outer surface of said fiber membrane and said lumen layer defining a lumen surface of said fiber membrane, wherein pores in said skin layer have an average pore size of less than about 7 nm, and pores in said lumen layer have an average pore size of from about 0.5 to about 3 μm mounted on said body and passing through said fluid chamber; and
a conduit in fluid communication with the tubules; and a conduit in fluid communication with said fluid chamber.

7. The cartridge of claim 6, comprising a first conduit in fluid communication with a first end of the lumen of the tubular fiber membrane in the tubule, a second conduit in fluid communication with a second end of the lumen of the tubular fiber membrane, and third and fourth conduits in fluid communication with said fluid chamber.

* * * * *